US011457817B2

(12) United States Patent
Sarvazyan

(10) Patent No.: US 11,457,817 B2
(45) Date of Patent: Oct. 4, 2022

(54) SYSTEMS AND METHODS FOR HYPERSPECTRAL ANALYSIS OF CARDIAC TISSUE

(71) Applicant: The George Washington University, Washington, DC (US)

(72) Inventor: Narine Sarvazyan, Potomac, MD (US)

(73) Assignee: The George Washington University, Washington, DC (US)

( * ) Notice: Subject to any disclaimer, the term of this patent is extended or adjusted under 35 U.S.C. 154(b) by 205 days.

(21) Appl. No.: 16/440,778

(22) Filed: Jun. 13, 2019

(65) Prior Publication Data

US 2020/0008681 A1 Jan. 9, 2020

Related U.S. Application Data

(63) Continuation of application No. 14/549,057, filed on Nov. 20, 2014, now abandoned.
(Continued)

(51) Int. Cl.
*A61B 5/00* (2006.01)
*A61B 90/00* (2016.01)
(Continued)

(52) U.S. Cl.
CPC .......... *A61B 5/0075* (2013.01); *A61B 5/0036* (2018.08); *A61B 5/0084* (2013.01);
(Continued)

(58) Field of Classification Search
CPC ...... A61B 18/1492; A61B 2017/00057; A61B 2017/00061; A61B 2018/00351;
(Continued)

(56) References Cited

U.S. PATENT DOCUMENTS 3,387,305 A  6/1968  Shafer
3,831,467 A  8/1974  Moore
(Continued)

FOREIGN PATENT DOCUMENTS

CN  1289239  3/2001
CN  1764419  4/2006
(Continued)

OTHER PUBLICATIONS

Office Action in U.S. Appl. No. 14/952,048 dated Jul. 8, 2020.
(Continued)

*Primary Examiner* — Mark D Remaly
(74) *Attorney, Agent, or Firm* — Greenberg Traurig, LLP; David J. Dykeman; Roman Fayerberg

(57) ABSTRACT

Systems and methods for hyperspectral analysis of cardiac tissue are provided. In some embodiments, a method for visualizing ablation lesions includes illuminating at one or more illumination wavelengths a surface of tissue having an ablation lesion; collecting a spectral data set comprising spectral images of the illuminated tissue acquired at multiple spectral bands each at one or more acquisition wavelengths; distinguishing between the ablation lesion and an unablated tissue based on one or more spectral differences between the ablation lesion and unablated tissue; and creating a composite image of the tissue showing the ablation lesion and the unablated tissue.

15 Claims, 25 Drawing Sheets

Related U.S. Application Data

(60) Provisional application No. 61/906,769, filed on Nov. 20, 2013.

(51) Int. Cl.
*A61B 18/02* (2006.01)
*A61B 18/00* (2006.01)
*A61B 17/00* (2006.01)
*A61B 18/14* (2006.01)

(52) U.S. Cl.
CPC ............ *A61B 90/37* (2016.02); *A61B 5/0071* (2013.01); *A61B 18/1492* (2013.01); *A61B 2017/00057* (2013.01); *A61B 2017/00061* (2013.01); *A61B 2018/00351* (2013.01); *A61B 2018/00357* (2013.01); *A61B 2018/0212* (2013.01); *A61B 2090/373* (2016.02); *A61B 2090/3735* (2016.02)

(58) Field of Classification Search
CPC .. A61B 2018/00357; A61B 2018/0212; A61B 2090/373; A61B 2090/3735; A61B 5/0036; A61B 5/0071; A61B 5/0075; A61B 5/0084; A61B 90/37
See application file for complete search history.

(56) References Cited

U.S. PATENT DOCUMENTS

| | | | |
|---|---|---|---|
| 4,024,873 | A | 5/1977 | Antoshkiw et al. |
| 4,619,247 | A | 10/1986 | Inoue et al. |
| 5,074,306 | A | 12/1991 | Green et al. |
| 5,187,572 | A | 2/1993 | Nakamura et al. |
| 5,350,375 | A | 9/1994 | Deckelbaum et al. |
| 5,419,323 | A | 5/1995 | Kittrell et al. |
| 5,421,337 | A | 6/1995 | Richards-Kortum et al. |
| 5,507,287 | A | 4/1996 | Palcic et al. |
| 5,540,681 | A | 7/1996 | Strul et al. |
| 5,584,799 | A | 12/1996 | Gray |
| 5,590,660 | A | 1/1997 | MacAulay et al. |
| 5,657,760 | A | 8/1997 | Ying et al. |
| 5,713,364 | A | 2/1998 | DeBaryshe et al. |
| 5,749,830 | A | 5/1998 | Kaneko et al. |
| 5,833,688 | A | 11/1998 | Sieben et al. |
| 5,885,258 | A | 3/1999 | Sachdeva et al. |
| 5,904,651 | A | 5/1999 | Swanson et al. |
| 5,954,665 | A | 9/1999 | Ben Haim |
| 6,064,069 | A | 5/2000 | Nakano et al. |
| 6,112,123 | A | 8/2000 | Kelleher et al. |
| 6,124,597 | A | 9/2000 | Shehada et al. |
| 6,174,291 | B1 | 1/2001 | McMahon et al. |
| 6,178,346 | B1 | 1/2001 | Amundson et al. |
| 6,197,021 | B1 | 3/2001 | Panescu et al. |
| 6,208,886 | B1 | 3/2001 | Alfano et al. |
| 6,217,573 | B1 | 4/2001 | Webster et al. |
| 6,219,566 | B1 | 4/2001 | Weersink et al. |
| 6,251,107 | B1 | 6/2001 | Schaer |
| 6,289,236 | B1 | 9/2001 | Koenig et al. |
| 6,309,352 | B1 | 10/2001 | Oraevsky et al. |
| 6,343,228 | B1 | 1/2002 | Qu |
| 6,423,055 | B1 | 7/2002 | Farr et al. |
| 6,423,057 | B1 | 7/2002 | He et al. |
| 6,450,971 | B1 | 9/2002 | Andrus et al. |
| 6,516,217 | B1 | 2/2003 | Tsujita |
| 6,522,913 | B2 | 2/2003 | Swanson et al. |
| 6,542,767 | B1 | 4/2003 | McNichols et al. |
| 6,572,609 | B1 | 6/2003 | Farr et al. |
| 6,584,360 | B2 | 6/2003 | Francischelli et al. |
| 6,626,900 | B1 | 9/2003 | Sinofsky et al. |
| 6,648,883 | B2 | 11/2003 | Francischelli et al. |
| 6,658,279 | B2 | 12/2003 | Swanson et al. |
| 6,663,622 | B1 | 12/2003 | Foley et al. |
| 6,663,627 | B2 | 12/2003 | Francischelli et al. |
| 6,671,535 | B1 | 12/2003 | McNichols et al. |
| 6,697,657 | B1 | 2/2004 | Shehada et al. |
| 6,706,038 | B2 | 3/2004 | Francischelli et al. |
| 6,716,196 | B2 | 4/2004 | Lesh et al. |
| 6,743,225 | B2 | 6/2004 | Sanchez et al. |
| 6,746,401 | B2 | 6/2004 | Panescu |
| 6,761,716 | B2 | 7/2004 | Kadhiresan et al. |
| 6,825,928 | B2 | 11/2004 | Liu et al. |
| 6,936,047 | B2 | 8/2005 | Nasab et al. |
| 6,937,885 | B1 | 8/2005 | Lewis et al. |
| 6,942,657 | B2 | 9/2005 | Sinofsky et al. |
| 6,953,457 | B2 | 10/2005 | Farr et al. |
| 6,974,454 | B2 | 12/2005 | Hooven |
| 6,975,898 | B2 | 12/2005 | Seibel |
| 6,975,899 | B2 | 12/2005 | Faupel et al. |
| 6,979,290 | B2 | 12/2005 | Mourlas et al. |
| 6,989,010 | B2 | 1/2006 | Francischelli et al. |
| 7,001,383 | B2 | 2/2006 | Keidar |
| 7,029,470 | B2 | 4/2006 | Francischelli et al. |
| 7,047,068 | B2 | 5/2006 | Haissaguerre |
| 7,130,672 | B2 | 10/2006 | Pewzner et al. |
| 7,192,427 | B2 | 3/2007 | Chapelon et al. |
| 7,207,984 | B2 | 4/2007 | Farr et al. |
| 7,232,437 | B2 | 6/2007 | Berman et al. |
| 7,235,045 | B2 | 6/2007 | Wang et al. |
| 7,250,048 | B2 | 7/2007 | Francischelli et al. |
| 7,252,664 | B2 | 8/2007 | Nasab et al. |
| 7,255,695 | B2 | 8/2007 | Falwell et al. |
| 7,289,205 | B2 | 10/2007 | Yaroslavsky et al. |
| 7,306,593 | B2 | 12/2007 | Keidar et al. |
| 7,338,485 | B2 | 3/2008 | Brucker et al. |
| 7,357,796 | B2 | 4/2008 | Farr et al. |
| 7,367,944 | B2 | 5/2008 | Rosemberg et al. |
| 7,367,972 | B2 | 5/2008 | Francischelli et al. |
| 7,497,858 | B2 | 3/2009 | Chapelon et al. |
| 7,527,625 | B2 | 5/2009 | Knight et al. |
| 7,534,204 | B2 | 5/2009 | Starksen et al. |
| 7,539,530 | B2 | 5/2009 | Caplan et al. |
| 7,587,236 | B2 | 9/2009 | Demos et al. |
| 7,591,816 | B2 | 9/2009 | Wang et al. |
| 7,596,404 | B2 | 9/2009 | Maier et al. |
| 7,598,088 | B2 | 10/2009 | Balas |
| 7,640,046 | B2 | 12/2009 | Pastore |
| 7,662,152 | B2 | 2/2010 | Sharareh et al. |
| 7,681,579 | B2 | 3/2010 | Schwartz |
| 7,727,229 | B2 | 6/2010 | He et al. |
| 7,727,231 | B2 | 6/2010 | Swanson |
| 7,729,750 | B2 | 6/2010 | Tromberg et al. |
| 7,766,907 | B2 | 8/2010 | Dando et al. |
| 7,776,033 | B2 | 8/2010 | Swanson |
| 7,822,460 | B2 | 10/2010 | Halperin et al. |
| 7,824,397 | B2 | 11/2010 | McAuley |
| 7,824,399 | B2 | 11/2010 | Francischelli et al. |
| 7,837,676 | B2 | 11/2010 | Sinelnikov et al. |
| 7,846,157 | B2 | 12/2010 | Kozel |
| 7,862,561 | B2 | 1/2011 | Swanson et al. |
| 7,877,128 | B2 | 1/2011 | Schwartz |
| 7,918,850 | B2 | 4/2011 | Govari et al. |
| 7,930,016 | B1 | 4/2011 | Saadat |
| 7,942,871 | B2 | 5/2011 | Thapliyal et al. |
| 7,950,397 | B2 | 5/2011 | Thapliyal et al. |
| 7,974,683 | B2 | 7/2011 | Balaset et al. |
| 7,976,537 | B2 | 7/2011 | Lieber et al. |
| 7,979,107 | B2 | 7/2011 | Lin et al. |
| 7,992,573 | B2 | 8/2011 | Wilson et al. |
| 7,996,078 | B2 | 8/2011 | Paul et al. |
| 8,007,433 | B2 | 8/2011 | Iketani |
| 8,024,027 | B2 | 9/2011 | Freeman et al. |
| 8,025,661 | B2 | 9/2011 | Arnold et al. |
| 8,050,746 | B2 | 11/2011 | Saadat et al. |
| 8,078,266 | B2 | 12/2011 | Saadat et al. |
| 8,123,742 | B2 | 2/2012 | Berger |
| 8,123,745 | B2 | 2/2012 | Beeckler et al. |
| 8,129,105 | B2 | 3/2012 | Zuckerman |
| 8,131,350 | B2 | 3/2012 | Saadat et al. |
| 8,137,333 | B2 | 3/2012 | Saadat et al. |
| 8,144,966 | B2 | 3/2012 | Provenzano et al. |
| 8,146,603 | B2 | 4/2012 | Thapliyal et al. |
| 8,147,484 | B2 | 4/2012 | Lieber et al. |
| 8,152,795 | B2 | 4/2012 | Farr et al. |

(56) References Cited

U.S. PATENT DOCUMENTS

| | | |
|---|---|---|
| 8,160,680 B2 | 4/2012 | Boyden et al. |
| 8,175,688 B2 | 5/2012 | Lewis et al. |
| 8,180,436 B2 | 5/2012 | Boyden et al. |
| 8,188,446 B2 | 5/2012 | Ohno |
| 8,195,271 B2 | 6/2012 | Rahn |
| 8,203,709 B2 | 6/2012 | Ishii |
| 8,219,183 B2 | 7/2012 | Mashke et al. |
| 8,221,310 B2 | 7/2012 | Saadat et al. |
| 8,235,985 B2 | 8/2012 | Saadat et al. |
| 8,241,272 B2 | 8/2012 | Arnold et al. |
| 8,267,926 B2 | 9/2012 | Paul et al. |
| 8,277,444 B2 | 10/2012 | Arnold et al. |
| 8,298,227 B2 | 10/2012 | Leo et al. |
| 8,309,346 B2 | 11/2012 | Zuckerman |
| 8,317,783 B2 | 11/2012 | Cao et al. |
| 8,333,012 B2 | 12/2012 | Rothe et al. |
| 8,353,907 B2 | 1/2013 | Winkler et al. |
| 8,357,149 B2 | 1/2013 | Govari et al. |
| 8,366,705 B2 | 2/2013 | Arnold et al. |
| 8,369,922 B2 | 2/2013 | Paul et al. |
| 8,374,682 B2 | 2/2013 | Freeman et al. |
| 8,382,750 B2 | 2/2013 | Brannan |
| 8,403,925 B2 | 3/2013 | Miller et al. |
| 8,414,508 B2 | 4/2013 | Thapliyal et al. |
| 8,417,321 B2 | 4/2013 | Saadat et al. |
| 8,417,323 B2 | 4/2013 | Uzunbajakava et al. |
| 8,419,613 B2 | 4/2013 | Saadat et al. |
| 8,435,232 B2 | 5/2013 | Aeby et al. |
| 8,444,639 B2 | 5/2013 | Arnold et al. |
| 8,460,285 B2 | 6/2013 | Wang et al. |
| 8,463,366 B2 | 6/2013 | Freeman et al. |
| 8,500,730 B2 | 8/2013 | Lee et al. |
| 8,504,132 B2 | 8/2013 | Friedman et al. |
| 8,511,317 B2 | 8/2013 | Thapliyal et al. |
| 8,540,704 B2 | 9/2013 | Melsky et al. |
| 8,548,567 B2 | 10/2013 | Maschke et al. |
| 8,556,892 B2 | 10/2013 | Hong et al. |
| 8,583,220 B2 | 11/2013 | Schwartz |
| 8,603,084 B2 | 12/2013 | Fish et al. |
| 8,607,800 B2 | 12/2013 | Thapliyal et al. |
| 8,628,520 B2 | 1/2014 | Sharareh et al. |
| 8,641,705 B2 | 2/2014 | Leo et al. |
| 8,641,706 B2 | 2/2014 | Lieber et al. |
| 8,690,758 B2 | 4/2014 | Matsumoto |
| 8,702,690 B2 | 4/2014 | Paul et al. |
| 8,709,008 B2 | 4/2014 | Willis et al. |
| 8,728,077 B2 | 5/2014 | Paul et al. |
| 8,755,860 B2 | 6/2014 | Paul et al. |
| 8,774,906 B2 | 7/2014 | Harks et al. |
| 8,808,281 B2 | 8/2014 | Emmons et al. |
| 8,849,380 B2 | 9/2014 | Patwardhan |
| 8,858,495 B2 | 10/2014 | Tegg et al. |
| 8,876,817 B2 | 11/2014 | Avitall et al. |
| 8,882,697 B2 | 11/2014 | Celermajer et al. |
| 8,894,589 B2 | 11/2014 | Leo et al. |
| 8,894,641 B2 | 11/2014 | Brannan |
| 8,900,219 B2 | 12/2014 | Sinofsky et al. |
| 8,900,225 B2 | 12/2014 | Bar-Tal et al. |
| 8,900,228 B2 | 12/2014 | Grunewald et al. |
| 8,900,229 B2 | 12/2014 | Govari et al. |
| 8,906,011 B2 | 12/2014 | Gelbart et al. |
| 8,915,878 B2 | 12/2014 | Winkler et al. |
| 8,923,959 B2 | 12/2014 | Boveja et al. |
| 8,926,604 B2 | 1/2015 | Govari et al. |
| 8,929,973 B1 | 1/2015 | Webb et al. |
| 8,948,851 B2 | 2/2015 | Leblond et al. |
| 8,951,247 B2 | 2/2015 | Ding et al. |
| 8,986,292 B2 | 3/2015 | Sliwa et al. |
| 8,986,298 B2 | 3/2015 | Lee et al. |
| 8,998,890 B2 | 4/2015 | Paul et al. |
| 8,998,892 B2 | 4/2015 | Winkler et al. |
| 8,998,893 B2 | 4/2015 | Avitall |
| 9,008,746 B2 | 4/2015 | Pastore et al. |
| 9,014,789 B2 | 4/2015 | Mercader et al. |
| 9,084,611 B2 | 7/2015 | Amirana et al. |
| 9,220,411 B2 | 12/2015 | Hillman |
| 9,233,241 B2 | 1/2016 | Long |
| 9,277,865 B2 | 3/2016 | Yamaguchi et al. |
| 10,076,238 B2 | 9/2018 | Amirana et al. |
| 10,143,517 B2 | 12/2018 | Ransbury et al. |
| 10,568,535 B2 | 2/2020 | Roberts et al. |
| 10,682,179 B2 | 6/2020 | Ransbury et al. |
| 10,716,462 B2 | 7/2020 | Amirana et al. |
| 10,722,301 B2 | 7/2020 | Amirana et al. |
| 10,736,512 B2 | 8/2020 | Mercader et al. |
| 10,779,904 B2 | 9/2020 | Ransbury et al. |
| 11,096,584 B2 | 8/2021 | Mercader et al. |
| 2002/0042556 A1 | 4/2002 | Sugimoto et al. |
| 2002/0123666 A1 | 9/2002 | Matsumoto |
| 2002/0143326 A1 | 10/2002 | Foley et al. |
| 2003/0028188 A1 | 2/2003 | Paddock et al. |
| 2003/0120142 A1 | 6/2003 | Dubuc et al. |
| 2003/0120144 A1 | 6/2003 | Grabek et al. |
| 2003/0208252 A1 | 11/2003 | O'Boyle et al. |
| 2004/0073206 A1 | 4/2004 | Foley et al. |
| 2004/0092806 A1 | 5/2004 | Sagon et al. |
| 2004/0097788 A1 | 5/2004 | Mourlas et al. |
| 2004/0138656 A1 | 7/2004 | Francischelli et al. |
| 2004/0187875 A1 | 9/2004 | He et al. |
| 2004/0215310 A1 | 10/2004 | Amirana |
| 2004/0267326 A1 | 12/2004 | Ocel et al. |
| 2005/0014995 A1 | 1/2005 | Amundson et al. |
| 2005/0043637 A1 | 2/2005 | Caplan et al. |
| 2005/0070987 A1 | 3/2005 | Erickson |
| 2005/0075629 A1 | 4/2005 | Chapelon et al. |
| 2005/0119523 A1 | 6/2005 | Starksen et al. |
| 2005/0119548 A1 | 6/2005 | Lin et al. |
| 2005/0197530 A1 | 9/2005 | Wallace et al. |
| 2005/0197623 A1 | 9/2005 | Leeflang et al. |
| 2005/0215899 A1 | 9/2005 | Trahey et al. |
| 2005/0228452 A1 | 10/2005 | Mourlas et al. |
| 2005/0251125 A1 | 11/2005 | Pless et al. |
| 2005/0283195 A1 | 12/2005 | Pastore et al. |
| 2006/0009756 A1 | 1/2006 | Francischelli et al. |
| 2006/0013454 A1 | 1/2006 | Flewelling et al. |
| 2006/0025760 A1 | 2/2006 | Podhajsky |
| 2006/0089636 A1 | 4/2006 | Christopherson et al. |
| 2006/0122583 A1 | 6/2006 | Pesach et al. |
| 2006/0122587 A1 | 6/2006 | Sharareh |
| 2006/0184048 A1 | 8/2006 | Saadat |
| 2006/0229515 A1 | 10/2006 | Sharareh et al. |
| 2006/0229594 A1 | 12/2006 | Franchichelli et al. |
| 2007/0015964 A1 | 1/2007 | Eversull et al. |
| 2007/0016079 A1 | 1/2007 | Freeman et al. |
| 2007/0016130 A1 | 1/2007 | Leeflang et al. |
| 2007/0038126 A1 | 2/2007 | Pyle et al. |
| 2007/0049827 A1 | 3/2007 | Donaldson et al. |
| 2007/0083217 A1 | 4/2007 | Eversull et al. |
| 2007/0167828 A1 | 7/2007 | Saadat |
| 2007/0185479 A1 | 8/2007 | Lau |
| 2007/0225697 A1 | 9/2007 | Shroff et al. |
| 2007/0270717 A1 | 11/2007 | Tang et al. |
| 2007/0270789 A1 | 11/2007 | Berger |
| 2007/0270792 A1 | 11/2007 | Hennemann et al. |
| 2007/0270795 A1 | 11/2007 | Francischelli et al. |
| 2007/0276259 A1 | 11/2007 | Okawa et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0015569 A1 | 1/2008 | Saadat et al. |
| 2008/0033241 A1 | 2/2008 | Peh et al. |
| 2008/0058650 A1 | 3/2008 | Saadat et al. |
| 2008/0058785 A1 | 3/2008 | Boyden et al. |
| 2008/0058786 A1 | 3/2008 | Boyden et al. |
| 2008/0097476 A1 | 4/2008 | Peh et al. |
| 2008/0101677 A1 | 5/2008 | Mashke et al. |
| 2008/0103355 A1 | 5/2008 | Boyden et al. |
| 2008/0119694 A1 | 5/2008 | Lee |
| 2008/0154257 A1 | 6/2008 | Sharareh et al. |
| 2008/0172049 A1 | 7/2008 | Bredno et al. |
| 2008/0183036 A1 | 7/2008 | Saadat et al. |
| 2008/0212867 A1 | 9/2008 | Provenzano et al. |
| 2008/0214889 A1 | 9/2008 | Saadat et al. |
| 2008/0221448 A1 | 9/2008 | Khuri-Yakub et al. |

(56) References Cited

U.S. PATENT DOCUMENTS

| | | |
|---|---|---|
| 2008/0228032 A1 | 9/2008 | Starksen et al. |
| 2008/0228079 A1 | 9/2008 | Donaldson et al. |
| 2008/0243214 A1 | 10/2008 | Koblish |
| 2008/0275300 A1 | 11/2008 | Rothe et al. |
| 2008/0281293 A1 | 11/2008 | Peh et al. |
| 2008/0300589 A1 | 12/2008 | Paul et al. |
| 2009/0012367 A1 | 1/2009 | Chin et al. |
| 2009/0030276 A1 | 1/2009 | Saadat et al. |
| 2009/0030412 A1 | 1/2009 | Willis et al. |
| 2009/0054803 A1 | 2/2009 | Saadat et al. |
| 2009/0062790 A1 | 3/2009 | Malchano et al. |
| 2009/0076373 A1 | 3/2009 | Maschke |
| 2009/0076375 A1 | 3/2009 | Maschke |
| 2009/0082623 A1 | 3/2009 | Rothe et al. |
| 2009/0082660 A1 | 3/2009 | Rahn et al. |
| 2009/0125022 A1 | 5/2009 | Saadat et al. |
| 2009/0131931 A1 | 5/2009 | Lee et al. |
| 2009/0143640 A1 | 6/2009 | Saadat et al. |
| 2009/0203962 A1 | 8/2009 | Miller et al. |
| 2009/0204069 A1 | 8/2009 | Hirszowicz et al. |
| 2009/0221871 A1 | 9/2009 | Peh et al. |
| 2009/0227999 A1 | 9/2009 | Willis et al. |
| 2009/0253991 A1 | 10/2009 | Balas et al. |
| 2009/0275799 A1 | 11/2009 | Saadat et al. |
| 2009/0281541 A1 | 11/2009 | Ibrahim et al. |
| 2009/0292211 A1 | 11/2009 | Lin et al. |
| 2009/0299354 A1 | 12/2009 | Melsky et al. |
| 2009/0299363 A1 | 12/2009 | Saadat et al. |
| 2009/0306643 A1 | 12/2009 | Pappone et al. |
| 2010/0022832 A1 | 1/2010 | Makiyama |
| 2010/0041986 A1 | 2/2010 | Nguyen et al. |
| 2010/0056966 A1 | 3/2010 | Toth |
| 2010/0081127 A1 | 4/2010 | Maier et al. |
| 2010/0081948 A1 | 4/2010 | Pastore et al. |
| 2010/0084563 A1 | 4/2010 | Ohno |
| 2010/0114094 A1 | 5/2010 | Thapliyal et al. |
| 2010/0130836 A1 | 5/2010 | Malchano et al. |
| 2010/0152728 A1 | 6/2010 | Park et al. |
| 2010/0198065 A1 | 8/2010 | Thapliyal et al. |
| 2010/0204544 A1 | 8/2010 | Takei |
| 2010/0204561 A1 | 8/2010 | Saadat |
| 2010/0228247 A1 | 9/2010 | Paul et al. |
| 2010/0241117 A1 | 9/2010 | Paul et al. |
| 2010/0274364 A1 | 10/2010 | Pacanowsky |
| 2010/0312094 A1 | 12/2010 | Guttman et al. |
| 2010/0312096 A1 | 12/2010 | Guttman et al. |
| 2010/0331838 A1 | 12/2010 | Ibrahim et al. |
| 2011/0009793 A1 | 1/2011 | Lucero |
| 2011/0019893 A1 | 1/2011 | Rahn et al. |
| 2011/0029058 A1 | 2/2011 | Swanson |
| 2011/0042580 A1 | 2/2011 | Wilson et al. |
| 2011/0066147 A1 | 3/2011 | He et al. |
| 2011/0071647 A1 | 3/2011 | Mahon |
| 2011/0082450 A1 | 4/2011 | Melsky et al. |
| 2011/0082451 A1 | 4/2011 | Melsky et al. |
| 2011/0082452 A1 | 4/2011 | Melsky et al. |
| 2011/0117025 A1 | 5/2011 | Dacosta et al. |
| 2011/0144524 A1 | 6/2011 | Fish et al. |
| 2011/0224494 A1 | 9/2011 | Piskun et al. |
| 2011/0230903 A1 | 9/2011 | Bertolero |
| 2011/0275932 A1 | 11/2011 | Leblond et al. |
| 2011/0276046 A1 | 11/2011 | Heimbecher et al. |
| 2011/0282250 A1 | 11/2011 | Fung et al. |
| 2011/0313417 A1 | 12/2011 | De La Rama et al. |
| 2012/0023638 A1 | 2/2012 | Leicester |
| 2012/0029504 A1 | 2/2012 | Afonso et al. |
| 2012/0109031 A1 | 5/2012 | Vollbrecht |
| 2012/0123276 A1 | 5/2012 | Govari et al. |
| 2012/0143177 A1 | 6/2012 | Avitall |
| 2012/0150046 A1 | 6/2012 | Watson et al. |
| 2012/0184812 A1 | 7/2012 | Terakawa |
| 2012/0184813 A1 | 7/2012 | Terakawa |
| 2012/0197243 A1 | 8/2012 | Sherman et al. |
| 2012/0215112 A1 | 8/2012 | Lewis et al. |
| 2012/0220999 A1 | 8/2012 | Long |
| 2012/0259263 A1 | 10/2012 | Celermajer et al. |
| 2012/0323237 A1 | 12/2012 | Paul et al. |
| 2012/0326055 A1 | 12/2012 | Wilson et al. |
| 2013/0006116 A1 | 1/2013 | Kim et al. |
| 2013/0030425 A1 | 1/2013 | Stewart et al. |
| 2013/0079645 A1 | 3/2013 | Amirana et al. |
| 2013/0085416 A1 | 4/2013 | Mest |
| 2013/0096593 A1 | 4/2013 | Thapliyal et al. |
| 2013/0096594 A1 | 4/2013 | Thapliyal et al. |
| 2013/0102862 A1 | 4/2013 | Amirana et al. |
| 2013/0107002 A1 | 5/2013 | Kikuchi |
| 2013/0137949 A1 | 5/2013 | Freeman et al. |
| 2013/0150693 A1 | 6/2013 | D'Angelo et al. |
| 2013/0150732 A1 | 6/2013 | Manzke et al. |
| 2013/0158545 A1 | 6/2013 | Govari et al. |
| 2013/0172742 A1 | 7/2013 | Rankin et al. |
| 2013/0172875 A1 | 7/2013 | Govari et al. |
| 2013/0226163 A1 | 8/2013 | Peled et al. |
| 2013/0237841 A1 | 9/2013 | Freeman et al. |
| 2013/0253330 A1 | 9/2013 | Demos |
| 2013/0261455 A1 | 10/2013 | Thapliyal et al. |
| 2013/0267875 A1 | 10/2013 | Thapliyal et al. |
| 2013/0281920 A1 | 10/2013 | Hawkins et al. |
| 2013/0282005 A1 | 10/2013 | Koch et al. |
| 2013/0289358 A1 | 10/2013 | Melsky et al. |
| 2013/0289672 A1 | 10/2013 | Hakomori et al. |
| 2013/0296840 A1 | 11/2013 | Condie et al. |
| 2013/0310680 A1 | 11/2013 | Werahera et al. |
| 2013/0331831 A1 | 12/2013 | Werneth et al. |
| 2014/0031802 A1 | 1/2014 | Melsky |
| 2014/0058244 A1 | 2/2014 | Krocak |
| 2014/0058246 A1 | 2/2014 | Boveja et al. |
| 2014/0081253 A1 | 3/2014 | Kumar et al. |
| 2014/0088418 A1 | 3/2014 | Radulescu et al. |
| 2014/0107430 A1 | 4/2014 | Deno et al. |
| 2014/0121537 A1 | 5/2014 | Aeby et al. |
| 2014/0121660 A1 | 5/2014 | Hauck |
| 2014/0148703 A1 | 5/2014 | Deladi et al. |
| 2014/0163360 A1 | 6/2014 | Stevens-Wright et al. |
| 2014/0163543 A1 | 6/2014 | Allison et al. |
| 2014/0171806 A1 | 6/2014 | Govari et al. |
| 2014/0171936 A1 | 6/2014 | Govari et al. |
| 2014/0180273 A1 | 6/2014 | Nair |
| 2014/0194867 A1 | 7/2014 | Fish et al. |
| 2014/0194869 A1 | 7/2014 | Leo et al. |
| 2014/0275972 A1 | 9/2014 | George et al. |
| 2014/0276687 A1 | 9/2014 | Goodman et al. |
| 2014/0276771 A1 | 9/2014 | Miller et al. |
| 2014/0316280 A1 | 10/2014 | Mueller et al. |
| 2014/0324085 A1 | 10/2014 | Thapliyal et al. |
| 2014/0350547 A1 | 11/2014 | Sharareh et al. |
| 2014/0357956 A1 | 12/2014 | Salahieh et al. |
| 2015/0038824 A1 | 2/2015 | Lupotti |
| 2015/0073245 A1 | 3/2015 | Klimovitch et al. |
| 2015/0099979 A1 | 4/2015 | Caves et al. |
| 2015/0141847 A1 | 5/2015 | Sarvazyan et al. |
| 2015/0164332 A1 | 6/2015 | Mercader et al. |
| 2015/0182279 A1 | 7/2015 | Ashton et al. |
| 2015/0196202 A1 | 7/2015 | Mercader et al. |
| 2015/0327753 A1 | 11/2015 | Amirana et al. |
| 2015/0346100 A1 | 12/2015 | Racowsky et al. |
| 2016/0051321 A1 | 2/2016 | Salahieh et al. |
| 2016/0120599 A1 | 5/2016 | Amirana et al. |
| 2016/0120602 A1 | 5/2016 | Ransbury et al. |
| 2016/0143522 A1 | 5/2016 | Ransbury et al. |
| 2017/0014202 A1 | 1/2017 | Ransbury et al. |
| 2017/0135559 A1 | 5/2017 | Horrisberger et al. |
| 2018/0263476 A1 | 9/2018 | Amirana et al. |
| 2019/0053849 A1 | 2/2019 | Ransbury et al. |
| 2020/0008681 A1 | 1/2020 | Sarvazyan |
| 2020/0352425 A1 | 11/2020 | Amirana et al. |
| 2020/0352644 A1 | 11/2020 | Ransbury et al. |
| 2020/0352645 A1 | 11/2020 | Amirana et al. |
| 2021/0045834 A1 | 2/2021 | Ransbury et al. |
| 2021/0205017 A1 | 7/2021 | Amirana et al. |

(56) References Cited

U.S. PATENT DOCUMENTS

| | | | |
|---|---|---|---|
| 2021/0369118 | A1 | 12/2021 | Sarvazyan |
| 2022/0031377 | A1 | 2/2022 | Ransbury et al. |

FOREIGN PATENT DOCUMENTS

| | | |
|---|---|---|
| CN | 101199410 | 6/2008 |
| CN | 102099671 | 6/2011 |
| CN | 102397104 | 4/2012 |
| CN | 203525125 | 4/2014 |
| CN | 106028914 | 10/2016 |
| DE | 102005021205 | 11/2006 |
| DE | 102011083522 | 3/2013 |
| EP | 2691041 | 2/2014 |
| EP | 2 889 013 | 7/2015 |
| JP | 60182928 | 9/1985 |
| JP | 63-262613 | 10/1988 |
| JP | 10150177 | 6/1998 |
| JP | 2006158546 | 6/2006 |
| JP | 20090148550 A | 7/2009 |
| JP | 2011/212423 | 10/2011 |
| JP | 20130544551 A | 12/2013 |
| JP | 20150128586 A | 7/2015 |
| NL | 2002010 | 10/2009 |
| WO | WO 1997/037622 | 10/1997 |
| WO | 1999013934 A1 | 3/1999 |
| WO | WO 2001/001854 | 1/2001 |
| WO | WO 2001/072214 | 10/2001 |
| WO | 2003092520 A1 | 11/2003 |
| WO | WO 2004/028353 | 4/2004 |
| WO | WO 2006/028824 | 3/2006 |
| WO | 2007041542 A2 | 4/2007 |
| WO | WO 2007/109554 | 9/2007 |
| WO | WO 2007/127228 | 11/2007 |
| WO | WO 2008/028149 | 3/2008 |
| WO | WO 2008/114748 | 9/2008 |
| WO | WO 2008/154578 | 12/2008 |
| WO | WO 2010/075450 | 7/2010 |
| WO | WO 2011/025640 | 3/2011 |
| WO | WO 2011/113162 | 9/2011 |
| WO | 2012038824 A1 | 3/2012 |
| WO | WO 2012/049621 | 4/2012 |
| WO | 2012067682 A1 | 5/2012 |
| WO | 20120131577 A2 | 10/2012 |
| WO | WO 2013/044182 | 3/2013 |
| WO | WO 2013/068885 | 5/2013 |
| WO | WO 2013/116316 | 8/2013 |
| WO | 2013169340 A1 | 11/2013 |
| WO | WO 2014/028770 | 2/2014 |
| WO | WO 2015/073871 | 5/2015 |
| WO | WO 2015/077474 | 5/2015 |
| WO | WO 2016/073476 | 5/2016 |
| WO | WO 2016/073492 | 5/2016 |
| WO | WO 2016/086160 | 6/2016 |
| WO | WO 2017/015257 | 1/2017 |

OTHER PUBLICATIONS

Office Action in U.S. Appl. No. 14/541,991 dated Oct. 20, 2020.
Office Action in U.S. Appl. No. 14/952,048 dated Oct. 30, 2019.
Office Action in U.S. Appl. No. 14/919,004 dated Jan. 7, 2020.
Office Action in U.S. Appl. No. 14/541,991 dated Mar. 19, 2020.
Anderson et al. "Real-time spectroscopic assessment of thermal damage: implications for radiofrequency ablation". J Gastrointest Surg. 2004; 8: 660-669.
Anderson, J.K., "Time Course of Nieotinamide Adenine Dinueleotide Diaphorase Staining after Renal Radiofrequeney Ablation Influences Viability Assessment", Journal of Endourology, vol. 21, Issue 2, Mar. 5, 2007.
Asfour et al, "Signal decomposition of transmembrane voltage-sensitive dye fluorescence using a multiresolution wavelet analysis" IEEE Trans Biomed Eng. 2011; 58: 2083-2093.
Berthier, J.P., et al., "XeC1 Laser Action at Medium Fluences on Biological Tissues: Fluorescence Study and Simulation with a Chemical Solution", Journal of Photochemistry and Photobiology B: Biology, vol. 5, Issues 3-4, pp. 495-503, May, 1990.
Boersma et al,."Pulmonary vein isolation by duty-cycled bipolar and unipolar radiofrequeney energy with a multielectrode ablation catheter". Heart Rhythm5:1635-1642, 2008.
Bogaards et al., In Vivo Quantification of Fluorescent Molecular Markers in Real-Time: A Review to Evaluate the Performance of Five Existing Methods, Photodiagnosis and Photodynamic Therapy, vol. 4: 170-178 (2007).
Bogaards et al., n Vivo Quantification of Fluorescent Molecular Markers in Real-Time by Ratio Imaging for Diagnostic Screening and Image-Guided Surgery, Lasers in Surgery and Medicing vol. 39: 605-613 (2007).
Buch et al. "Epicardial catheter ablation of atrial fibrillation." Minerva Med. 2009; 100: 151-157.
Cancio et al., "Hyperspectral Imaging: A New Approach to the Diagnosis of Hemorrhagic Shock", The Journal of Trauma, 2006, vol. 60, No. 5: 1087-1095.
Chance et al, "Fluorescence measurements of mitochondrial pyridine nucleotide in aerobiosis and anaerobiosis" Nature. 1959; 184: 931-4.
Coremans et al, "Pretransplantation assessment of renal viability with NADH fluorimetry", Kidney International, vol. 57, (2000), pp. 671-683.
d'Avila A. "Epicardial catheter ablation of ventricular tachycardia." Heart Rhythm. 2008; 5: S73-5.
Demos et al, "Real time assessment of RF cardiac tissue ablation with optical spectroscopy", Opt Express. 2008; 16: 15286-15296.
Dickfeld et al, "Characterization of Radiofrequency Ablation Lesions With Gadolinium-Enhanced Cardiovascular Magnetic Resonance Imaging" J Am Coll Cardiol. 2006; 47: 370-378.
Dukkipati et al, "Visual balloon-guided point-by-point ablation: reliable, reproducible, and persistent pulmonary vein isolation", Circ Arrhythm Electrophysiol. 2010; 3: 266-273.
Dumas et al, "Myocardial electrical impedance as a predictor of the quality of RF-induced linear lesions." Physiol Meas. 2008; 29: 1195-1207.
Dyer, B., et al., Heart, "The Application of Autofluorescence Lifetime Metrology as a Novel Label-free Technique for the Assessment of Cardiac Disease", vol. 11, Issue Supplement 3, pp. 186, Jun. 2014.
Fleming et al, "Real-time monitoring of cardiac redio-frequency ablation lesion formation using an optical coherence tomography forward-imaging catheter", Journal of Biomedical Optics, May/Jun. 2010, vol. 15(3).
Fleming et al, "Toward guidance of epicardial cardiac radiofrequency ablation therapy using optical coherence tomography" J Biomed Opt. 2010; 15: 041510.
Girard et al, "Contrast-enhanced C-arm CT evaluation of radiofrequency ablation lesions in the left ventricle", JACC Cardiovasc Imaging. 2011; 4: 259-268.
Grimard et al, "Percutaneous epicardial radiofrequency ablation of ventricular arrhythmias after failure of endocardial approach: a 9-year experience" J Cardiovasc Electrophysiol. 2010; 21: 56-61.
Henz et al, "Simultaneous epicardial and endocardial substrate mapping and radiofrequency catheter ablation as first-line treatment for ventricular tachycardia and frequent ICD shocks in chronic chagasic cardiomyopathy" J Interv Card Electrophysiol. 2009; 26: 195-205.
Himel et al, "Translesion stimulus-excitation delay indicates quality of linear lesions produced by radiofrequency ablation in rabbit hearts", Physiol Meas. 2007; 28: 611-623.
Kalman, J.M., et al., "Cardiac Magnetic Resonance Imaging to Detect Non-Contiguous Scar Following Atrial Fibrillation Ablation: Identifying our Knowledge Gaps", European Heart Journal, Editorial, pp. 1-3, Feb. 26, 2014.
Kay et al, "Locations of ectopic beats coincide with spatial gradients of NADH in a regional model of low-flow reperfusion", Am J Physiol Heart Circ Physiol. 2008; 294: H2400-5.
Khoury et al., "Localizing and Quantifying Ablation Lesions in the Left Ventricle by Myocardial Contrast Echocardiography", J Cardiovasc Electrophysiol. 2004; 15: 1078-1087.

(56) References Cited

OTHER PUBLICATIONS

Kim et al, "Materials for multifunctional balloon catheters with capabilities in cardiac electrophysiological mapping and ablation therapy", Nat Mater. 2011; 10: 316-323.
Kistler, P.M., et al., "The Impact of CT Image Integration into an Electroanatomic Mapping System on Clinical Outcomes of Catheter Ablation of Atrial Fibrillation", Journal of Cardiovascular Electyrophysiology, vol. 17, Issue 10, pp. 1093-1101, Oct. 2006.
Lardo, et al "Visualization and temporal/spatial characterization of cardiac radiofrequency ablation lesions using magnetic resonance imaging", Circulation. 2000; 102: 698-705.
Li, "Multiphoton Microscopy of Live Tissues with Ultraviolet Autofluorescence", IEEE Journal of Selected Topic in Quantam Electronics , in May/Jun. 2010, vol. 16, Issue 3, pp. 516-513.
Lo et al, "Three-dimensional electroanatomic mapping systems in catheter ablation of atrial fibrillation", Circ J. 2010; 74: 18-23.
Malchano, Z.J., "Integration of Cardiac CT/MR Imaging with Three-Dimensional Electroanatomical Mapping to Guide Catheter Manipulation in the Left Atrium: Implications for Catheter Ablation of Atrial Fibrillation", Journal of Cardiovascular Electrophysiology, vol. 17, Issue 11, pp. 1221-1229, Nov. 2006.
Mayevsky et al. "Oxidation-reduction states of NADH in vivo: from animals to clinical use", Mitochondrion. 2007; 7: 330-339.
Melby et al, "Atrial fibrillation propagates through gaps in ablation lines: implications for ablative treatment of atrial fibrillation", Heart Rhythm. 2008; 5: 1296-1301.
Menes et al, "Laparoscopy: searching for the proper insufflation gas" Surg Endosc. 2000; 14: 1050-1056.
Meng et al "A comparative study of fibroid ablation rates using radio frequency or high-intensity focused ultrasound", Cardiovasc Intervent Radiol. 2010; 33: 794-799.
Mercader et al, "NADH as an Endogenous Marker of Cardiac Tissue Injury at the Site of Radiofrequency Ablation", The George Washington University, Washington DC, Mar. 18, 2011.
Mercader et al, "Use of endogenous NADH fluorescence for real-time in situ visualization of epicardial radiofrequency ablation lesions and gaps", Am J Physiol Heart Circ Physiol, May 2012; 302(10): H2131-H2138.
Naito, H., et al., "Use of Nadh Fluorescence Imaging for Early Detection of Energy Failure and a Prediction of Infarction", Critical Care Medicine, vol. 39, Issue 12, pp. 40, Dec. 2011.
Nath et al, "Basic aspects of radiofrequency catheter ablation", J Cardiovasc Electrophysiol. 1994; 5: 863-876.
Niu et al, "An acute experimental model demonstrating 2 different forms of sustained atrial tachyarrhythmias". Circ Arrhythm Electrophysiol. 2009; 2: 384-392.
Perez et al. "Effects of gap geometry on conduction through discontinuous radiofrequency lesions" Circulation. 2006; 113: 1723-1729.
Ranji et al, "Fluorescence spectroscopy and imaging of myocardial apoptosis", Journal of Biomedical Optics 11(6), 064036 (Nov./Dec. 2006).
Ranji et al, "Quantifying Acute Myocardial Injury Using Ratiometric Fluorometry", IEEE Trans Biomed. Eng. May 2009; 56(5): 1556-1563.
Riess et al, "Altered NADH and improved function by anesthetic and ischemic preconditioning in guinea pig intact hearts", Am J Physiol Heart Circ Physiol 283; H53-H60, Mar. 14, 2002.
Robertson, J.O., "Quantification of the Functional Consequences of Atrial Fibrillation and Surgical Ablation on the Left Atrium Using Cardiac Magnetic Resonance Imaging", European Journal of Cardio-Thoracic Surgery, vol. 46, Issue 4, pp. 720-728, Oct. 1, 2014.
Roger et al, "American Heart Association Stastics Committee and Stroke Subcommittee. Heart disease and stroke statistics—2011 update; a report from American Heart Association", Circulation 2011; 123: e18-e209.
Sethuraman et al., "Spectroscopic Intravascular Photoacoustic Imaging to Differentiate Atherosclerotic Plaques", Optics Express, vol. 16, No. 5, pp. 3362-3367, Mar. 3, 2008.

Smith, S., et al., "Imaging Appearances Following Thermal Ablation", Clinical Radiology, vol. 63, Issue 1, pp. 1-11, Jan. 2008.
Sosa et al, "Epicardial mapping and ablation techniques to control ventricular tachycardia". J Cardiovasc Electrophysiol. 2005; 16: 449-452.
Sra, J., et al., "Computed Tomography-Fluoroscopy Image Integration-Guided Catheter Ablation of Atrial Fibrillation", Journal of Cardiovascular Electrophysiology, vol. 18, Issue 4, pp. 409-414, Apr. 2007.
Swartling et al, "Changes in tissue optical properties due to radio-frequency ablation of myocardium", Med Biol Eng Comput. 2003; 41: 403-409.
Swift et al, "Controlled regional hypoperfusion in Langendorff heart preparations". Physiol Meas. 2008; 29: 269-79.
Swift, L.M., et al., "Properties of Blebbistatin for Cardiac Optical Mapping and Other Imaging Applications", European Journal of Physiology, vol. 464, Issue 5, pp. 503-512, Nov. 2012.
Swift, Luther Mitchell, "Real-Time Visualization of Cardiac Ablation Lesions Using Endogenous NADH Fluorescence and Reflected Light", a dissertation submitted to the Faculty of the Columbian College of Arts and Sciences of The George Washington University in partial fulfillment of the requirements for the degree of Doctor of Philosophy, Jul. 23, 2013.
Van Haesendonck C, Sinnaeve A, Willems R, Vandenbulcke F, Stroobandt R, ."Biophysical and electrical aspects of radiofrequency catheter ablation". Acta Cardiol 50: 105-115, 1995.
Vetterlein et al, "Extent of damage in aschemic, nonreperfused myocardium of anesthetized rats", Am J Physiol Heart Circ Physiol 285: H755-H765, 2003.
Vo-Dinh et al., "A Hyperspectral Imaging System for In Vivo Optical Diagnostics", IEEE Engineering in Medicine and Biology Magazine, pp. 40-49, Sep./Oct. 2004.
Weight, C.J., et al., "Correlation of Radiographic Imaging and Histopathology Following Cryoablation and Radio Frequency Ablation for Renal Tumors", The Journal of Urology, vol. 179, Issue 4, pp. 1277-1283, Apr. 2008.
Wu, H., et al., "Real-Time Monitoring of Radiofrequency Ablation and Postablation Assessment: Accuracy of Contrast-Enhanced US in Experimental Rat Liver Model", Radiology, vol. 270, No. 1, pp. 107-116, Jan. 2014.
Yokoyama et al, "Novel contact force sensor incorporated in irrigated radiofrequency ablation catheter predicts lesion size and incidence of steam pop and thrombus", Circ Arrhythm Electrophysiol. 2008; 1: 354-362.
Zuzak et al., "Characterization of a Near-Infrared Laparoscopic Hyperspectral Imaging System for Minimally Invasive Surgery", Analytical Chemistry, vol. 79, No. 12, pp. 4709-4715, Jun. 15, 2007.
International Search Report based on PCT/US2012/056771 dated Dec. 3, 2012.
Office Action in U.S. Appl. No. 13/624,899 dated Oct. 2, 2014.
Office Action in U.S. Appl. No. 13/624,902 dated Oct. 2, 2014.
International Search Report dated Feb. 12, 2015 for PCT/US2014/066660.
European Search Report completed May 26, 2015 for EP 12 83 4435.
International Search Report dated Feb. 19, 2015 for PCT/US2014/065774.
International Search Report dated Jan. 19, 2016 for PCT/US2015/058824.
International Search Report dated Feb. 1, 2016 for PCT/US2015/062732.
International Search Report dated Feb. 4, 2016 for PCT/US2015/058851.
Office Action in U.S. Appl. No. 14/689,475 dated Apr. 6, 2016.
Office Action in U.S. Appl. No. 14/541,991 dated Jun. 22, 2016.
Office Action in U.S. Appl. No. 14/541,991 dated Feb. 28, 2017.
Office Action in U.S. Appl. No. 14/689,475 dated Apr. 13, 2017.
Office Action in U.S. Appl. No. 14/541,991 dated Jul. 13, 2017.
Office Action in U.S. Appl. No. 14/689,475 dated Aug. 23, 2017.
Office Action in U.S. Appl. No. 14/622,477 dated Oct. 5, 2017.
Office Action in U.S. Appl. No. 14/931,325 dated Mar. 22, 2018.
Office Action in U.S. Appl. No. 14/931,262 dated Apr. 20, 2018.
Office Action in U.S. Appl. No. 14/622,477 dated Jun. 5, 2018.

(56) References Cited

OTHER PUBLICATIONS

Office Action in U.S. Appl. No. 14/549,057 dated Jun. 15, 2018.
European Search Report completed Jun. 8, 2018 for EP 15 86 3645.
Office Action in U.S. Appl. No. 14/952,048 dated Aug. 27, 2018.
Office Action in U.S. Appl. No. 14/931,262 dated Aug. 28, 2018.
Office Action in U.S. Appl. No. 14/541,991 dated Sep. 13, 2018.
Office Action in U.S. Appl. No. 15/986,970 dated Sep. 17, 2018.
Office Action in U.S. Appl. No. 14/549,057 dated Dec. 13, 2018.
Office Action in U.S. Appl. No. 14/622,477 dated Dec. 19, 2018.
Office Action in U.S. Appl. No. 15/986,970 dated Jan. 10, 2019.
Office Action in U.S. Appl. No. 14/931,262 dated Jan. 11, 2019.
Office Action in U.S. Appl. No. 16/167,933 dated Jan. 11, 2019.
Office Action in U.S. Appl. No. 14/541,991 dated Jan. 24, 2019.
Office Action in U.S. Appl. No. 14/952,048 dated Mar. 1, 2019.
Office Action in U.S. Appl. No. 14/919,004 dated Apr. 4, 2019.
Office Action in U.S. Appl. No. 14/931,262 dated Aug. 22, 2019.
Office Action in U.S. Appl. No. 14/622,477 dated Sep. 5, 2019.
Office Action in U.S. Appl. No. 15/986,970 dated Sep. 16, 2019.
Office Action in U.S. Appl. No. 16/167,933 dated Sep. 25, 2019.
Extended European Search Report dated Feb. 20, 2019 for EP 16 828 397.6.
International Search Report based on PCT/US2021/012836 dated Apr. 1, 2021.
Office Action in U.S. Appl. No. 14/952,048 dated Jun. 9, 2021.

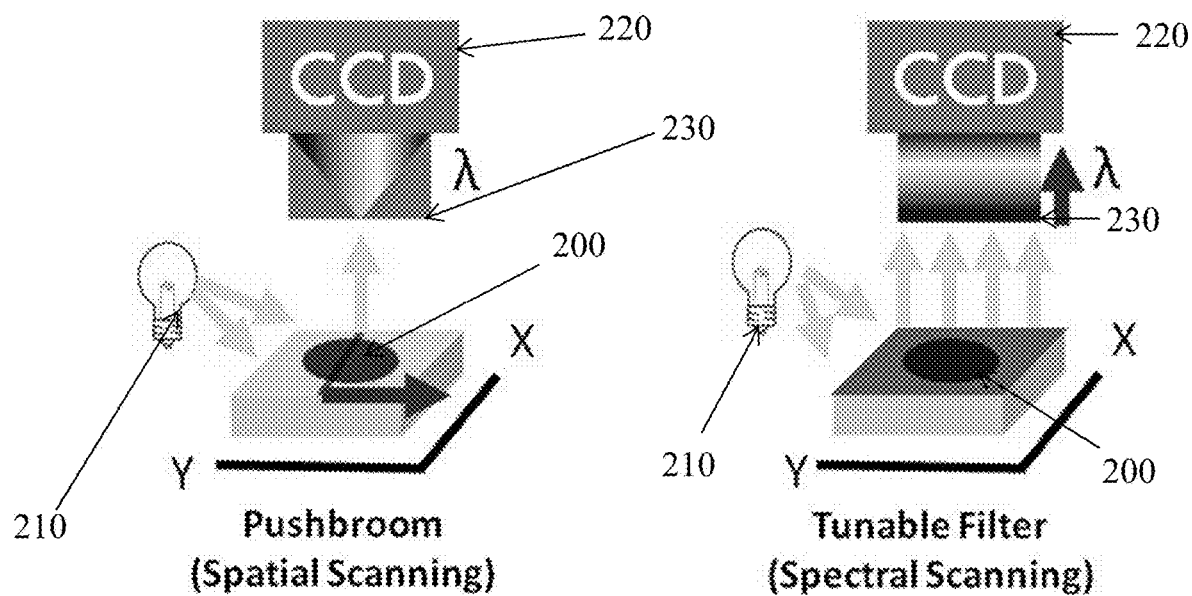
FIG. 2A
FIG. 2B
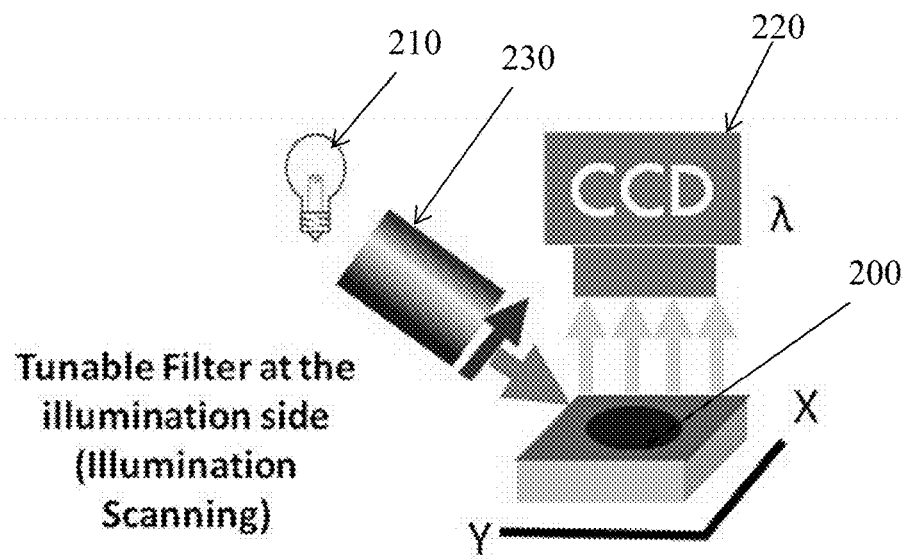
FIG. 2C

Composite Image with regions of interest

UVA illumination (365nm)

Lesion component

Non-ablated component

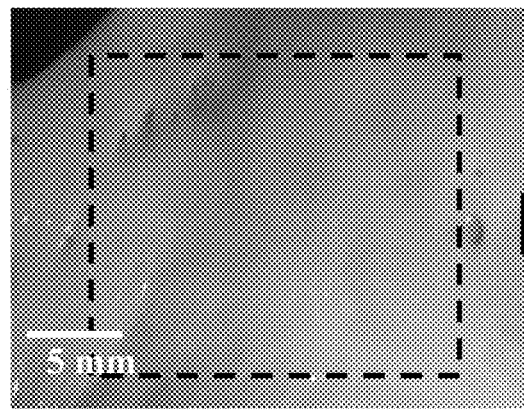
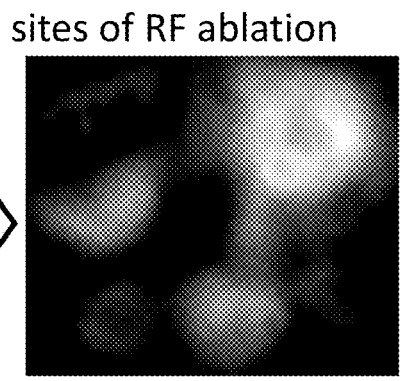
FIG. 12A　　　　　　　　FIG. 12B
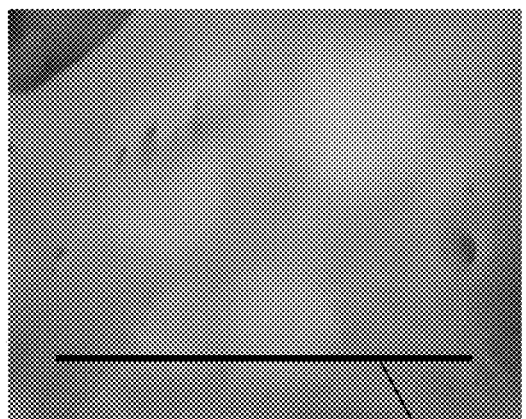
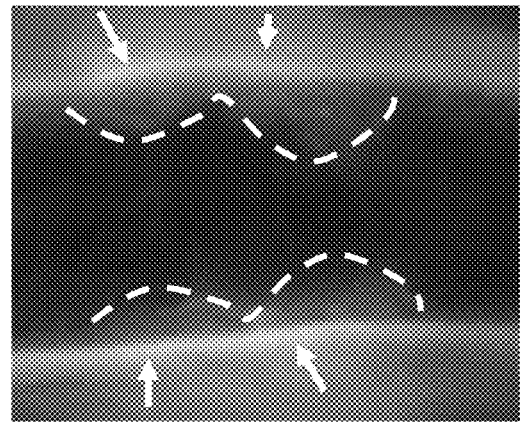
FIG. 12C　　　　　　　　FIG. 12D
1220

SYSTEMS AND METHODS FOR HYPERSPECTRAL ANALYSIS OF CARDIAC TISSUE

RELATED APPLICATIONS

This application is a continuation of U.S. application Ser. No. 14/549,057, filed on Nov. 20, 2014, which claims the benefit of and priority to U.S. Provisional Application Ser. No. 61/906,769, filed on Nov. 20, 2013, which applications are incorporated herein by reference in their entireties.

FIELD

The present disclosure generally relates to optical imaging to reveal structures of effected biological tissue within biological specimens for biomedical purposes. In particular, the present disclosure relates to devices, systems and methods of hyperspectral or multispectral modality for the identification and visualization of cardiac ablation lesions.

BACKGROUND

Atrial fibrillation (AF) is the most common sustained arrhythmia. In the United States alone, AF is projected to affect over 10 million people by the year 2050. AF accounts for one third of all hospital admissions for cardiac rhythm disturbances. AF is associated with increased mortality, morbidity and an impaired quality of life. Its incidence sharply increases with age. It is an independent risk factor for stroke, as it increases stroke probability by fivefold. AF prevalence increases significantly with age. Annual costs related to the management of AF in the US alone are approximately $7 billion. These costs consistently rank AF as leading public health expenditure.

Radiofrequency ablation (RFA), laser ablation and cryo ablation are the most common technologies of catheter-based mapping and ablation systems used by physicians to treat atrial fibrillation. Physician uses a catheter to direct energy to either destroy focal triggers or to form electrical isolation lines isolating the triggers from the heart's remaining conduction system. The latter technique is commonly used in what is called pulmonary vein isolation (PVI). However, the success rate of the AF ablation procedure has remained relatively stagnant with estimates of recurrence to be as high as 50% one-year post procedure. The most common reason for recurrence after catheter ablation is one or more gaps in the PVI lines. The gaps are usually the result of ineffective or incomplete lesions that may temporarily block electrical signals during the procedure but heal over time and facilitate the recurrence of atrial fibrillation.

To perform radiofrequency (RF) or cryo ablation procedures, a catheter is threaded into the heart and the tip is guided into the atria. A transseptal puncture is then performed to crossover from the right atrium into the left atrium where the crux of the ablation is performed. The most common treatment of AF consists of placing ablation lesions in a circular fashion around the ostium of pulmonary veins to isolate ectopic sources from the rest of the atria. Cryoablation involves freezing target tissue with the same ultimate goal to destroy abnormal sources of activity.

It believed surgical ablation when compared to pharmacological treatment provides the patient for a longer term of survival. Yet, the ablation surgery is often needed to be performed multiple times due to the lack of complete isolation of abnormal source from the tissue. Recurrence rate of AF after ablation surgery reaches as high as 50%, of which 90% of culprits can be linked to gaps between ablation lesions. These viable gaps can occur largely due to an inability of the surgeon to directly visualize tissue damage while performing percutaneous AF ablations. Whether the surgeon's goal is to complete pulmonary vein isolation with no gaps or site-targeted ablation, it is critical to know the degree of tissue damage at the site of the ablation. This is because the extent of tissue damage beneath the catheter is not a simple function of applied energy, for example, it depends on many factors including: contact between the catheter tip and the tissue, the thickness of the myocardium, the degree of blood flow nearby, the presence of fatty tissue and collagen and other factors.

Identification of gaps in prior circumferential ablation is possible with MRI technology; however an MRI cannot be done in real time in current EP labs. Thus, there is a need in the art for a device that provides for in vivo, real time analysis of the area that is being ablated. There is a need for a device that provides for high resolution visualization of lesion boundary, quantitative determinations of the gaps between the lesions and the lesion depth. There is a further need for a device that allows determination of the presence of scarred tissue at previously ablated sites in order to avoid re-ablating the same area As of today, ablations are performed in essentially 'blind' fashion, with electrical isolation of focal sources being the main indicator of ablation efficiency. There are at least two limitations of this approach. The first one is that the extent of the lesions cannot be measured during the procedure. The second is that the specific cause of electrical isolation cannot be determined. It may result from tissue necrosis, functional changes in reversibly injured cells, as well as by temporary edema. In the case of edema, it will subside after a few weeks, potentially restoring electrical conduction between the pulmonary veins and the left atrium and the return of AF. Indeed, despite an initial return to sinus rhythm after ablation therapy, AF has a high degree of recurrence.

Therefore, there is need, among many needs, in reducing the number of times for ablation surgery due to the lack of complete isolation of abnormal source from the tissue by providing better ways in forming and verifying proper lesions in real time and overall. Further, there is at least one need in improving ablation procedures by having real-time in-surgery visualization of lesions and gaps between them.

SUMMARY

Systems and methods for hyperspectral analysis of cardiac tissue are provided.

According to embodiments, devices, systems and methods of the present disclosure hyperspectral imaging can be used as a tool to distinguish between ablated and unablated atrial tissue based on spectral differences between the two. At least one method of the present disclosure employs spectral unmixing of a hyperspectral hypercube dataset to reveal the sites of thermal ablations and gaps between the ablated and unablated atrial tissue.

In some aspects, there is provided a method for visualizing ablation lesions that includes illuminating at one or more illumination wavelengths a surface of tissue having an ablation lesion; collecting a spectral data set comprising spectral images of the illuminated tissue acquired at multiple spectral bands each at one or more acquisition wavelengths; distinguishing between the ablation lesion and an unablated tissue based on one or more spectral differences between the ablation lesion and unablated tissue; and creating a composite image of the tissue showing the ablation lesion and the unablated tissue.

In some aspects, there is provided a method for visualizing atrial ablation lesion that includes illuminating one or more discrete illumination wavelengths a surface of heart tissue having an ablation lesion; collecting a spectral data from the illuminated heart tissue; distinguishing between the ablation lesion and an unablated tissue based on one or more spectral differences between the ablation lesion and unablated tissue; and creating an image of the heart tissue illustrating ablated tissue and unablated tissue.

In some aspects, there is provided a system for imaging tissue that includes a catheter having a distal region and a proximal region; a light source; an optical fiber extending from the light source to the distal region of the catheter to illuminate a tissue having a lesion site in proximity to the distal end of the catheter; an image bundle for collecting light reflected from the illuminated tissue; a camera connected to the image bundle, the camera being configured to gather hyperspectral data comprising spectral images of the illuminated tissue acquired at multiple spectral bands or at each illumination wavelength; an image processing unit in communication with the camera, the unit being configured to distinguish between the ablation lesion and an unablated tissue based on one or more spectral differences between the ablation lesion and unablated tissue and creating an image of the heart tissue illustrating the ablated tissue and the unablated tissue.

In some aspects, there is provided a system for imaging heart tissue that includes an illumination device configured to illuminate a tissue having a lesion site; an imaging device configured to gather hyperspectral data; an image processing unit in communication with the imaging device, the image processing unit configured to processing gathered hyperspectral data to generate an image that reveals the lesion site, wherein the generated image enabling to distinguish between an ablation lesion and an unablated tissue based on one or more spectral differences between the ablation lesion and unablated tissue and creating an resulting image of the heart tissue illustrating the ablated tissue and the unablated tissue.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 2A illustrates an embodiment of a system of the present disclosure with a pushbroom (spatial scanning) system.

FIG. 2B illustrates an embodiment of a system of the present disclosure with a turnable filter.

FIG. 2C illustrates an embodiment of a system of the present disclosure a turnable filter at the illumination side.

FIG. 7C shows the endocardial surface of the excised fresh human atria with cuts to show muscle tissue beneath. FIG. 7D shows the human atrial tissue stained with triphenyltetrazolium chloride (TTC), wherein cross sections show darkly stained muscle layers and white collagen layer on the endocardial side.

FIG. 8A, FIG. 8B, FIG. 8C and FIG. 8D illustrate imaging lesion boundaries with a HSI system, wherein FIG. 8A and FIG. 8B show visual appearances of the lesions, FIG. 8C and FIG. 8D illustrate lesions identified by Hyperspectral Imaging (HSI) approach.

FIG. 9A shows a visual appearance of the tissue, wherein FIG. 9B shows the individual components revealed by HSI cube principal component analysis (lesion sites 900, collagen 910, and muscle 920). Tissue was illuminated with incandescent white light; the reflected light was acquired within 450-950 nm range using 20 nm steps.

FIG. 10A illustrates a visual appearance of the tissue with regions of interest used to decompose a HSI cube into individual components. FIGS. 10B-10C show images of a muscle, collagen and lesions, respectively.

FIG. 11A shows a visual appearance of tissue under UV illumination, FIG. 11B shows a HSI composite image, and FIG. 11C and FIG. 11D show individual components revealed by principal component analysis. FIG. 11C shows the individual components revealed by principal component analysis including lesion component. FIG. 11D shows the individual components revealed by principal component analysis including non-ablated component.

FIG. 12A, FIG. 12B, FIG. 12C and FIG. 12D show an image of excised human left atria with four RF lesions of different strengths.

FIG. 13A upper shows a single deep lesion and corresponds to the 3D surface plot below it, and FIG. 13B upper illustrates two lesions of different depths with unablated tissue and the corresponding 3D plot below them, the unablated tissue is what appears as an elevation between the two lesion depths.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure generally relates to using hyperspectral and/or multispectral modality for identification and visualization of cardiac ablation lesions. In particular, using hyperspectral imaging as a tool to distinguish between ablated and unablated atrial tissue based on spectral differences between the two.

Due to the hearts different types of tissues and tissue structures, the aspect of revealing sites of thermal ablations and gaps between the ablated and unablated atrial tissue can be very complex and challenging to overcome.

According to embodiments of the present disclosure, a method for visualizing ablation lesions, the method includes illuminating at one or more illumination wavelengths a surface of tissue having an ablation lesion. Collecting a spectral data set comprising spectral images of the illuminated tissue acquired at multiple spectral bands each at different acquisition wavelengths. Distinguishing between the ablation lesion and an unablated tissue based on one or more spectral differences between the ablation lesion and unablated tissue. Finally, and creating a composite image of the tissue showing the ablated tissue and the unablated tissue.

In some embodiments, the present systems and methods may be employed to visualize ablated lesions in heart tissue (endocardial, epicardial, atrial and ventricular tissue). However, the presently disclosed methods and systems may also be applicable for analyzing lesions in other tissue types. The lesions to be analyzed may be created by ablation during ablation procedure. In some embodiments, existing lesions, created by ablation or by other means, may also be analyzed using methods and systems disclosed herein.

Figure 1A:
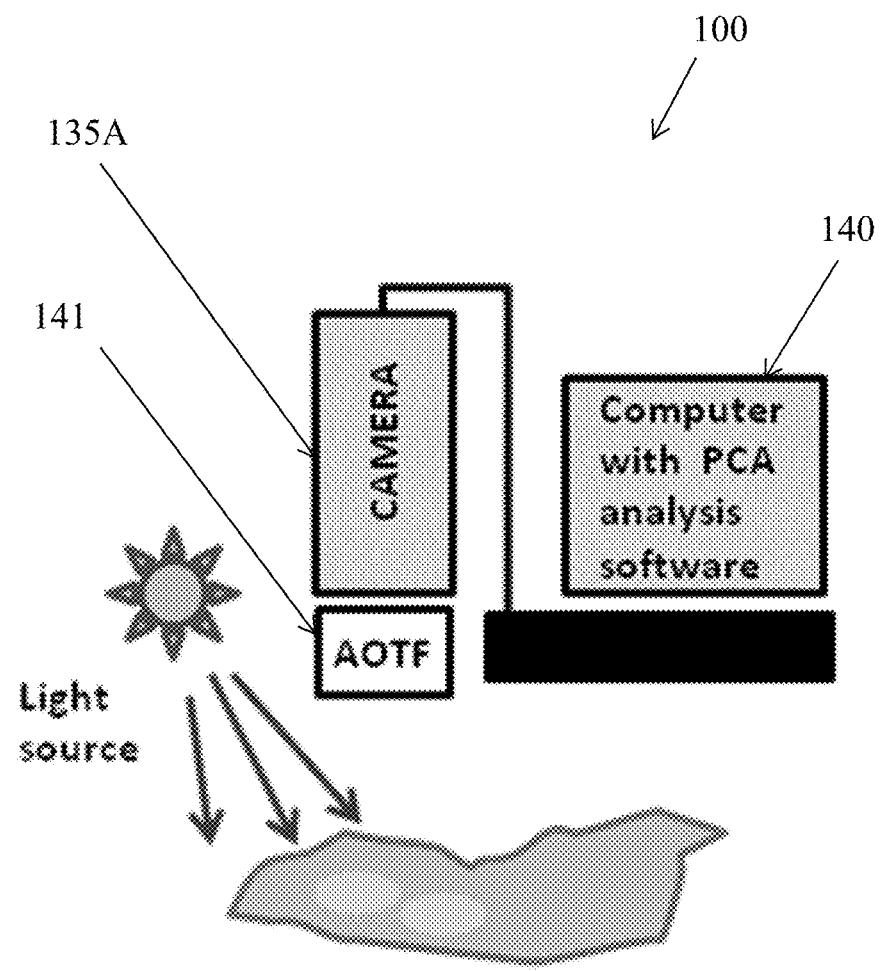
FIG. 1A illustrates a hyperspectral imaging (HSI) system with an acousto-optical tunable filter (AOTF) along with software (i.e. principal component analysis software (PCA)).
Figure 1B:
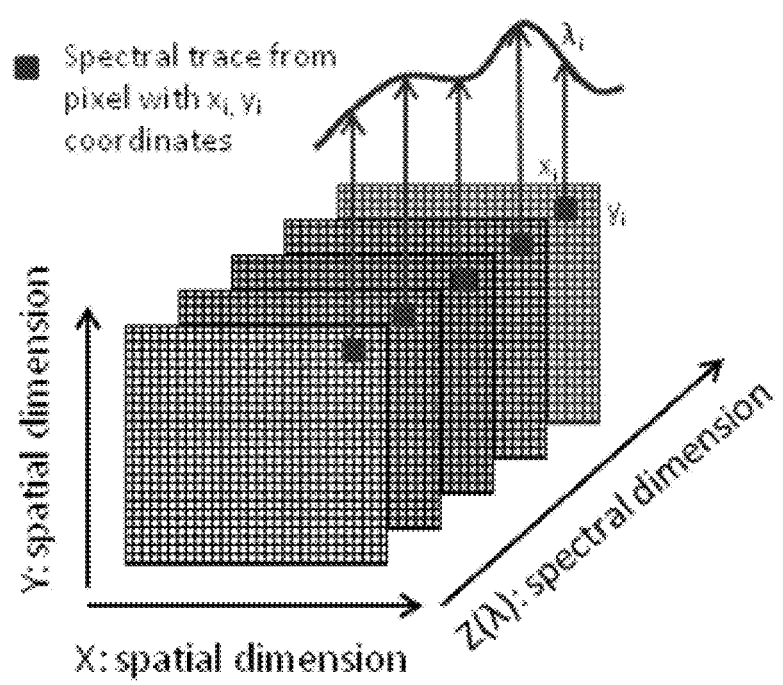
FIG. 1B illustrates a sequence of x-y images acquired at different wavelengths to create hyperspectral data cube.

FIG. 1A and FIG. 1B illustrate Hyperspectral Imaging (HSI) that is based on collecting and storing individual tissue images across multiple spectral bands. For example, FIG. 1A illustrates the components of HSI 100 which include a camera 135A, an acousto-optical tunable filter (AOTF) 141 along with a computer 140 having software, i.e. principal component analysis software (PCA)). Typically, when there are more than 10 spectral bands it is called hyperspectral, and when there are less than 10 spectral bands it is called multispectral. The HSI device used includes the math that decides what images are to be displayed and in what order is based on an Independent Component Analysis (PCA), but with a few proprietary modifications specific to the Nuance software (and Maestro, which is a whole animal imaging system based on the same technology). Please note, that the PCA algorithm can be used or another commercially available similar type of program could be used. However, the user chooses which images to be used to calculate spectra. Each image is thresholded to form a mask of positive/negative pixels. Those masks are compared and only unique regions are kept (if two images have the same pixels in their mask those pixels are discarded). After that the spectra within the remaining regions are averaged and a typical "compute pure spectrum" calculation is done, using the spectrum and the mixed spectrum.

Still referring to FIG. 1A and FIG. 1B, Hyperspectral Imaging (HSI) involves acquisition of a three-dimensional dataset called hypercube, with two spatial dimensions and one spectral dimension and it can be accomplished using different hardware configurations. FIG. 1B illustrates a sequence of x-y images acquired at different wavelengths (i.e. UV, visible and near-infrared wavelengths), that creates the hyperspectral data cube, wherein the spectral information from each pixel is then used to classify the pixels into different subtypes. HSI can visualize ablation lesions in both atrial and ventricular tissue, as well as provide visualization of healed lesions which results in tissue scarring. The methods and systems of the present disclosure are suitable for identifying lesions created by various types of ablation, including, but not limited to, laser, microwave, focused ultrasound induced lesion, acute cryo and radiofrequency. Delineation of lesion boundary and estimates of lesion depth are based on revealing changes in spectral properties of ablated regions. This is accomplished by acquiring images of ablated areas with specific ranges of UV, visible and near-infrared light and analysis of spectrum of a sample at each point in the imaging plane. Spectra from each pixel are then matched to existing spectral libraries, or are subjected to principal component analysis or related algorithms. Aspects include real-time in vivo analysis of the area that is being ablated, including high resolution visualization of lesion boundary, quantitative determination of the gaps between the lesions and an estimate of lesions depth. It will also provide determination of the presence of scarred tissue at previously ablated sites to avoid re-ablation of the same area. Some improvement include shortening the time and improving the efficiency of thermal ablation for treatment of AF, and minimize unnecessary tissue injury, which can lead to post-ablation complications such as pulmonary vein stenosis and esophageal injury, including erythema, ulcers and, in worst case scenario, left atrial—esophageal fistulas, and decrease post-ablation recurrence of AF and the need for multiple hospital readmissions for repeated ablations.

FIG. 2A, FIG. 2B and FIG. 2C show different optical configurations that can be used to collect hyperspectral information, wherein one or more may be used. For example, FIG. 2A illustrates an optical configuration that is enabled to collect hyperspectral information, a detector-based Hyperspectral Imaging (HSI) system that can be built using a movement of the object or the acquisition device such as a push-broom system. FIG. 2B illustrates an optical configuration that is enabled to collect hyperspectral information, a detector-based HSI system that can be built using static devices with tunable filters or a filter wheel. In these configurations, the tissue 200 may be illuminated from a light source 210 with a light having an illumination wavelength. The camera 220 may be equipped with a light modifier 230, such as a filter or a prism, to collect from the illuminated tissue 200 light having an acquisition wavelength at different spectral bands. FIG. 2C is illustrates an alternative source-based HSI approach, where it is a wavelength of illuminating light that is being changed, while a camera records whatever light is being transmitted to it. In such embodiments, the tissue 200 is illuminated with lights 210 having various spectral bands or wavelength (due to the filter or preselected light source), and the camera 220 collects all light from the illuminated tissue.

Referring to FIG. 2A, FIG. 2B and FIG. 2C, the spatially resolved spectral imaging obtained by HSI can provide diagnostic information about the tissue physiology, morphology, and composition. The spectra from each pixel can be classified into different subsets using principal component analysis or other mathematical algorithms referred hereafter as spectral unmixing. Thus, according to aspects of the present disclosure spectral un-mixing of hyperspectral hypercube dataset can reveal the sites of thermal ablations and gaps between them. Alternatively, they can be matched to pre-existing spectral libraries. Further, pixels with spectra that match the target spectrum to a specified level of confidence are then marked as potential targets. It is possible to use the one or more different optical configurations that collect hyperspectral information in combination as well as with pre-existing spectral libraries.

Cardiac tissue has a thick layer of collagen on both endo and epicardial sides that covers layers of muscle. This is particularly true for human left atria, which is the most clinically relevant site that is usually ablated to stop progression of atrial fibrillation. At least one aspect of any surgical ablation is to stop arrhythmias and inflict damage to muscle layers lying beneath the collagen layers. Yet collagen, white and highly fluorescent, masks most of the optical changes that accompany thermal ablations. Therefore, in cases when layer of collagen exceeds 100 microns, ablation-induced damage to the muscle is not readily visible to a naked eye. However, ablation alters spectral signature of the ablated tissue. Some spectral changes may include, but are not limited to, loss of the NADH fluorescence best reveals itself at about 350 nm to about 370 nm illumination and about 450 nm to 480 nm emission ranges, but is not limited to these ranges; a decrease in collagen fluorescence best reveals itself at about 330 nm to 360 nm illumination and about 430 nm to 460 nm emission ranges, but is not limited to these ranges; an increase in tissue scattering can lead to a larger amount of photons returning to the imaging detector that have lower energy than that of illuminating light. It is noted that this effect can be largely wavelength-independent and can occur across UV, visible and IR ranges. The result of it can be an elevated shoulder of a reflectance spectrum.

An increase in optical tissue density can be due to heat-induced tissue drying. It is noted that this effect can be largely wavelength-independent and can occur across UV, visible and IR ranges. Change in absorption can be due to e.g., myoglobin to methmyoglobin and other intercellular chromophore transitions. Accordingly, the presently disclosed systems and methods can take advantage of these changes to distinguish between ablated tissue and unablated tissue.

Figure 3A:
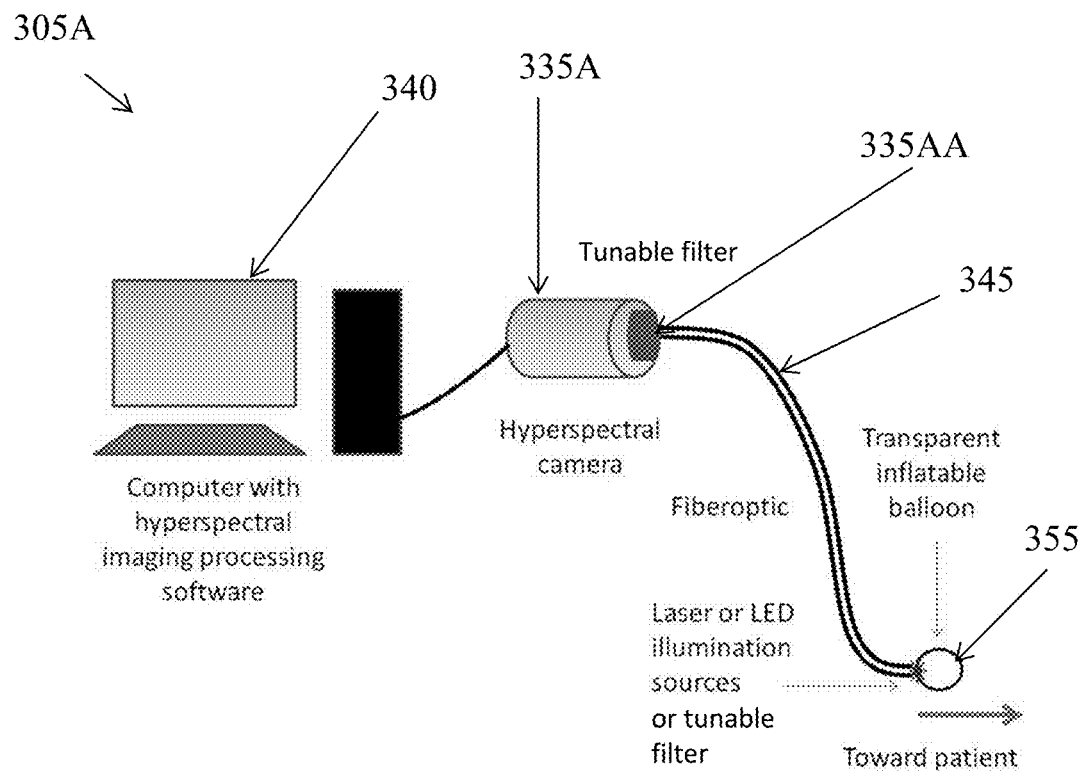
FIG. 3A illustrates a diagram showing at least one design of clinical catheter and hyperspectral imaging components according to aspects of the present disclosure.

FIG. 3A illustrates a diagram showing at least one design of clinical catheter 305A and hyperspectral imaging components according to aspects of the present disclosure. The diagram of FIG. 3A shows a visualization catheter 305A for live visualization of RF ablation lesions and gaps during percutaneous ablation procedure. The catheter 305A can include a computer 340, a light source (not shown), a camera 335A with a turnable filter 335AA, and a fiberoptic cable 345. In some embodiments, an inflatable balloon 355 may be included to displace blood between the fiberoptic cable 345 and the tissue surface. The fiberoptic cable 345 is then connected to a hyperspectral camera 335A. An increasing number of commercial hyperspectral cameras and related imaging processing software packages are now available. Most recent ones allows 30 different spectral bands or greater to be captured in parallel at video rate speed and to be analyzed in real-time with principle component analysis discrimination algorithms. The above described hyperspectral visualization catheter 305A can be also combined with RF or cryo ablator making it a single catheter 305A.

According to aspects of the present disclosure, the systems and methods may be extended from the above-described thermal lesions, i.e. RF and cryoinjury, to visualization of ablation lesions made by other means, such as laser-based, microwave or focused ultrasound based tissue destruction.

Figure 3B:
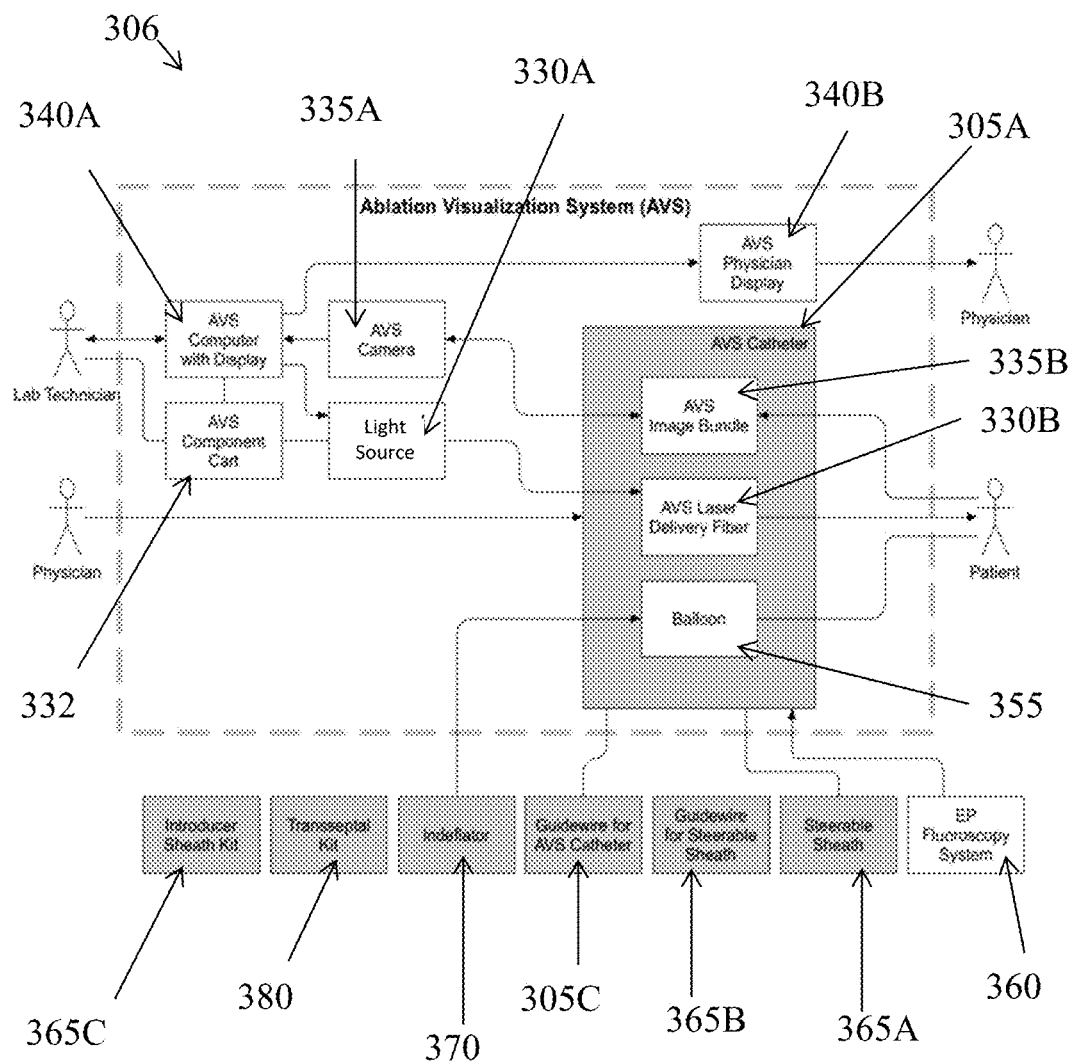
FIG. 3B illustrates a system architecture diagram of an embodiment system of the present disclosure.
Figure 3C:
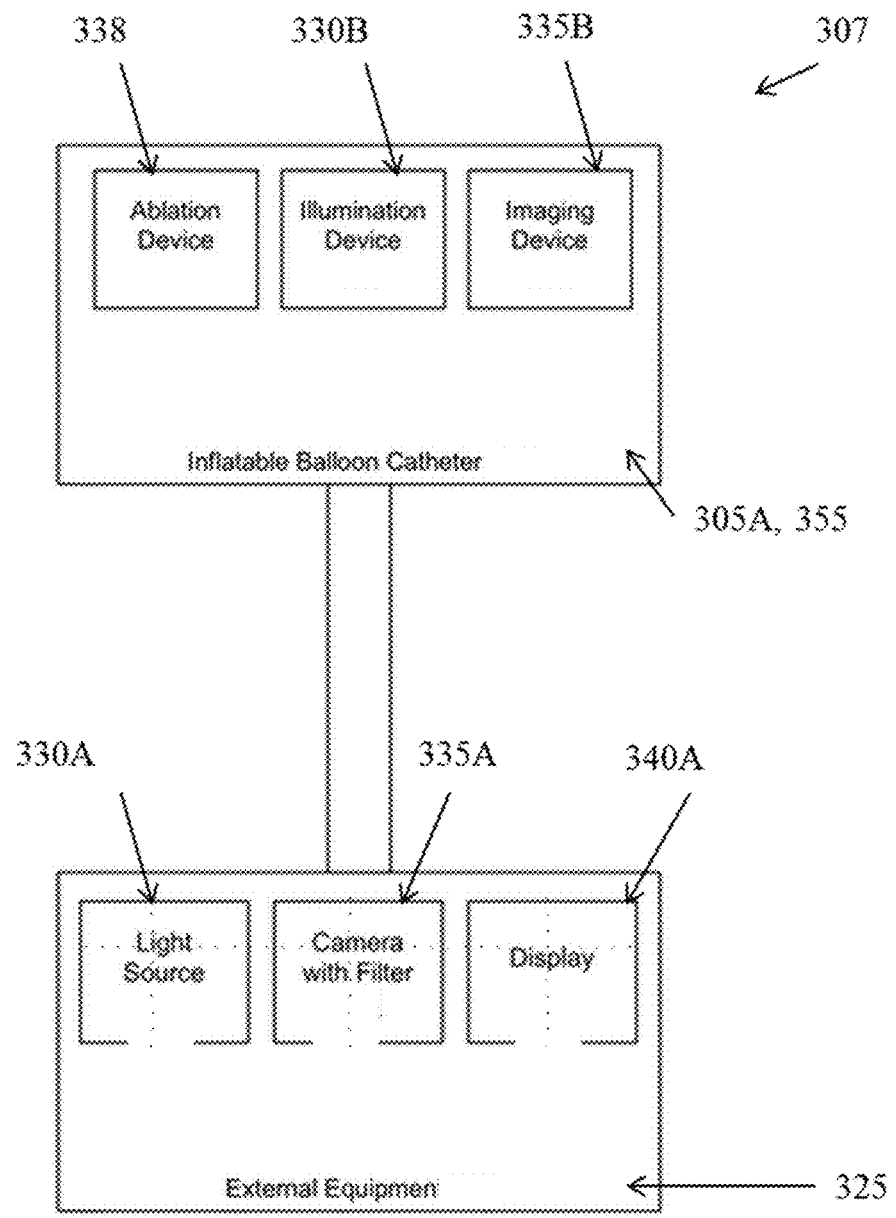
FIG. 3C illustrates a block diagram of an embodiment system of the present disclosure.

FIG. 3B and FIG. 3C illustrate diagrams showing an ablation visualization system (AVS) that incorporates hyperspectral imaging components as noted in FIG. 3A, according to some aspects of the present disclosure. FIG. 3B shows at least one embodiment of an ablation visualization system (AVS) 306 that incorporates hyperspectral imaging components as noted in FIG. 3A. FIG. 3C shows at least another embodiment of an ablation visualization system (AVS) 307 that incorporates hyperspectral imaging components as noted in FIG. 3A. FIG. 3B and FIG. 3C show a light source 330A that is external to the body of a patient and a light delivery fiber 330B for delivering light from the light source 330A to within the body of the patient, a camera 335A with appropriate filtering, if necessary, and an image bundle 335B connected to the camera, and a computer system 340 having one or more displays 340A (for a technician) and 340B (for a physician) with image processing software on its processor or controller. Aspects of the camera will be further discussed.

Figure 3D:
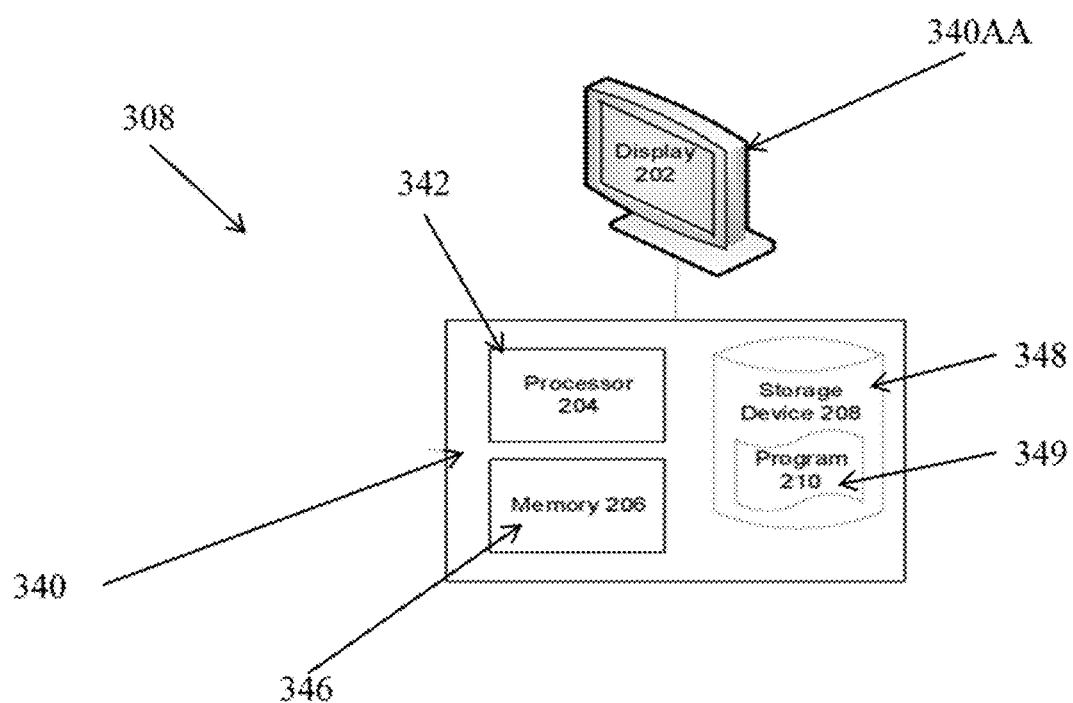
FIG. 3D illustrates a diagram showing an exemplary computer system suitable for use with the methods and systems of the present disclosure.

FIG. 3D shows, by way of example, a diagram of a typical processing architecture 308, which may be used in connection with the methods and systems of the present disclosure. A computer processing device 340 can be coupled to display 340AA for graphical output. Processor 342 can be a computer processor 342 capable of executing software. Typical examples can be computer processors (such as Intel® or AMD® processors), ASICs, microprocessors, and the like. Processor 342 can be coupled to memory 346, which can be typically a volatile RAM memory for storing instructions and data while processor 342 executes. Processor 342 may also be coupled to storage device 348, which can be a non-volatile storage medium, such as a hard drive, FLASH drive, tape drive, DVDROM, or similar device. Although not shown, computer processing device 340 typically includes various forms of input and output. The I/O may include network adapters, USB adapters, Bluetooth radios, mice, keyboards, touchpads, displays, touch screens, LEDs, vibration devices, speakers, microphones, sensors, or any other input or output device for use with computer processing device 340. Processor 342 may also be coupled to other type of computer-readable media, including, but are not limited to, an electronic, optical, magnetic, or other storage or transmission device capable of providing a processor, such as the processor 342, with computer-readable instructions. Various other forms of computer-readable media can transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Program 349 can be a computer program or computer readable code containing instructions and/or data, and can be stored on storage device 348. The instructions may comprise code from any computer-programming language, including, for example, C, C++, C#, Visual Basic, Java, Python, Perl, and JavaScript. In a typical scenario, processor 204 may load some or all of the instructions and/or data of program 349 into memory 346 for execution. Program 349 can be any computer program or process including, but not limited to web browser, browser application, address registration process, application, or any other computer application or process. Program 349 may include various instructions and subroutines, which, when loaded into memory 346 and executed by processor 342 cause processor 342 to perform various operations, some or all of which may effectuate the methods for managing medical care disclosed herein. Program 349 may be stored on any type of non-transitory computer readable medium, such as, without limitation, hard drive, removable drive, CD, DVD or any other type of computer-readable media.

It is possible the light source 330A may include a cart 332. In some embodiments, the system may further include a specialty catheter 305A comprising an inflatable balloon 355. In some embodiments, the image bundle 335B and the light delivery fiber may extend from the outside of the catheter 305A to a distal region of the catheter 305A inside the balloon 355. It is contemplated that there could be multiple components of each component added to the above disclosed system. The system may further include a guidewire for the catheter 305C, a EP Fluoroscopy System 360, a steerable sheath 365A, a guidewire for steerable sheath 365B, an introducer sheath kit 365C, an indeflator 370 and a transeptal kit 380.

FIG. 3C is a block diagram of an exemplary system in accordance with the present disclosure. The AVS system includes external equipment 325 having a light source 330A, a camera 335A with appropriate filtering, if necessary, and a computer system (not shown) having one or more displays 340A with image processing software. The AVS system includes internal equipment including an ablation device 338, an illumination device 330B and an imaging device 335B, wherein the internal components are within an internal balloon 355 associated with a catheter 305A. It is noted that the internal equipment including the catheter 305A with an inflatable balloon catheter 355, 305A is coupled to external equipment 325. In some embodiments, the illumination device 330B and an imaging device 335B may utilize a fiber-optic waveguide to pass the light to and from the treated tissue.

Still referring to FIG. 3B and FIG. 3C, the light source 330A may be selected to illuminate the tissues, such as an endocardial surface of the heart, at various wavelengths.

According to some aspects of FIG. 3B and FIG. 3C, a laser generated light may provide much more power for illumination and its wavelength can be pure at whatever number of nanometers that may be required. There are sources of commercial lasers that can emit in a desired illumination band and they are available in many power settings near 50 to 200 mW and higher. The instant system, in some embodiments, uses a laser with adjustable power up to 150 mW.

Still referring to FIG. 3B and FIG. 3C, the catheter 305A can be employed to perform many functions including, without limitations, vascular navigation, blood displacement, propagation of light from the light source 330A to the myocardium, and image gathering of the fluorescence light. One example of a suitable catheter 305A is disclosed in jointly-owned U.S. application Ser. No. 13/624,902, which is incorporated herein in its entirety. In some embodiments, the ablation technology is housed with or incorporated within the system and catheter 305A embodiment.

Figure 3E:
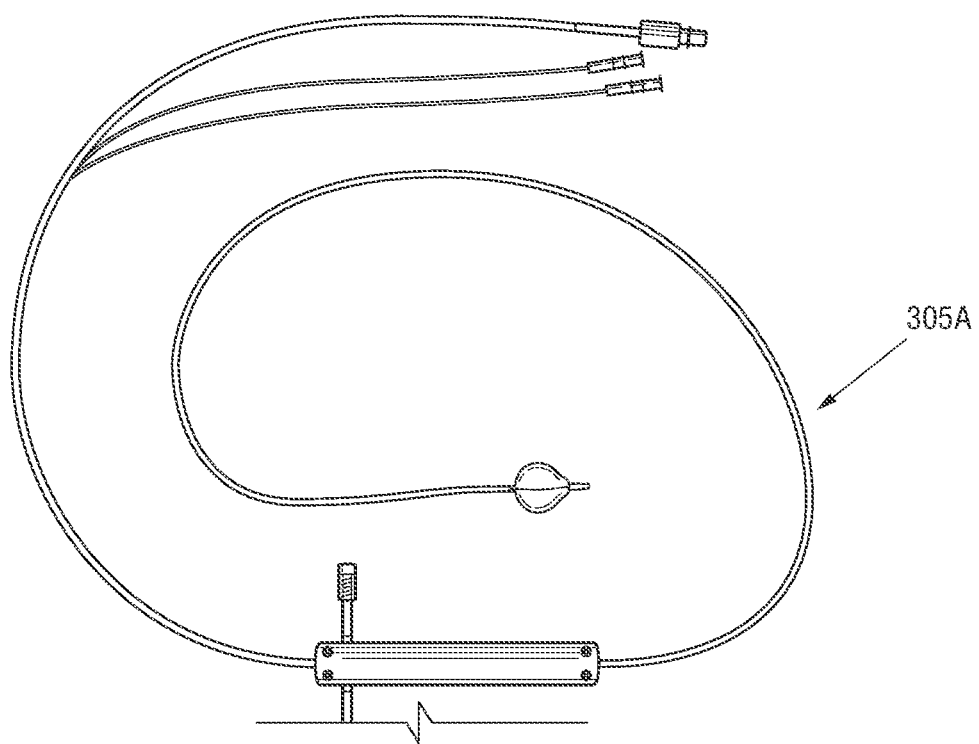
FIG. 3E illustrates a view of a specialty catheter in accordance with an embodiment of the present disclosure.
Figure 3F:
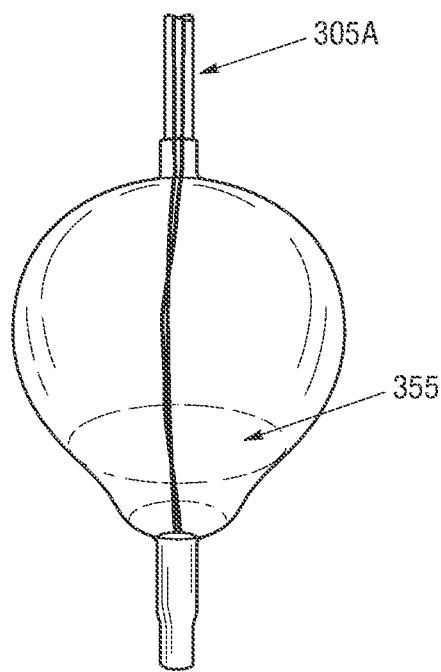
FIG. 3F illustrates a close-up photo of an inflated catheter balloon and tip in accordance with an aspect of the present disclosure.

In reference to FIG. 3E and FIG. 3F, the catheter 305A may include a balloon 355 at or near the distal end of the catheter 305A. Since blood absorbs the illumination and fluorescence wavelengths, the balloon 355 may displace blood from the myocardial surface. To do so, the balloon 355 may be expandable and compliant to seat well within the anatomy—especially the pulmonary veins. The medium used to inflate the balloon 355 may also be optically transparent and yet ideally be fluoroscopically opaque for navigation purposes. Suitable inflation medium include, but are not limited to, Deuterium (heavy water) and $CO_2$, which meet both requirements. The balloon 355 may also be constructed of a material that is optically clear in at least the wavelengths of concern for both illumination of the myocardium and fluorescence. The balloon 355 may be either, made of non-compliant materials but with optimally variable sizes of best fit into pulmonary veins and other structures, or, made of a compliant material such as silicone or urethane. In some embodiments, the balloon 355 may be optically transparent in the UV range of 330 nm to 370 nm.

In some embodiments, the balloon 355 is optically clear from 330 nm to 370 nm for UV illumination and from 400 nm to 500 nm for the fluorescence wavelengths. Suitable UV-transparent materials for the balloon 355 include, but are not limited to, silicone and urethane.

Still referring to FIG. 3E and FIG. 3F, the catheter 305A may also be used to efficiently deliver the illuminating light from the external light source 330A to the balloon 355 and out of the balloon 355 to the heart tissue. In some embodiments, a laser delivery fiber, usually made of quartz due to its UV efficiency and small diameter, may be used to deliver illuminating light from a UV laser light source.

The catheter 305A of FIG. 3E and FIG. 3F may also be employed to collect and transfer the light from the illuminated tissue to an external camera. In some embodiments, this may be accomplished via an imaging fiber bundle extending from the distal region of the catheter 305A to the external camera. In some embodiments, the image bundle may include one or more of individual, single-mode fibers that together maintain image integrity while transporting it along the length of the catheter 305A to a camera and a filter, as necessary. The imaging bundle, though flexible and small in diameter, may be able to achieve a sufficient field of view for imaging the target tissue area covered by the balloon 355.

The camera 335A, can be connected to the computer system 340 for receiving the light from the illuminated tissue for use in connection with the HSI method. In some embodiments, the digital image that is produced by the camera 335A is used to do the 2D and 3D reconstruction. In some embodiments, the image bundle may be connected to the camera 335A, the camera 335A may generate a digital image from the light received from the illuminated tissue, which can be displayed on the computer.

Figure 4A:
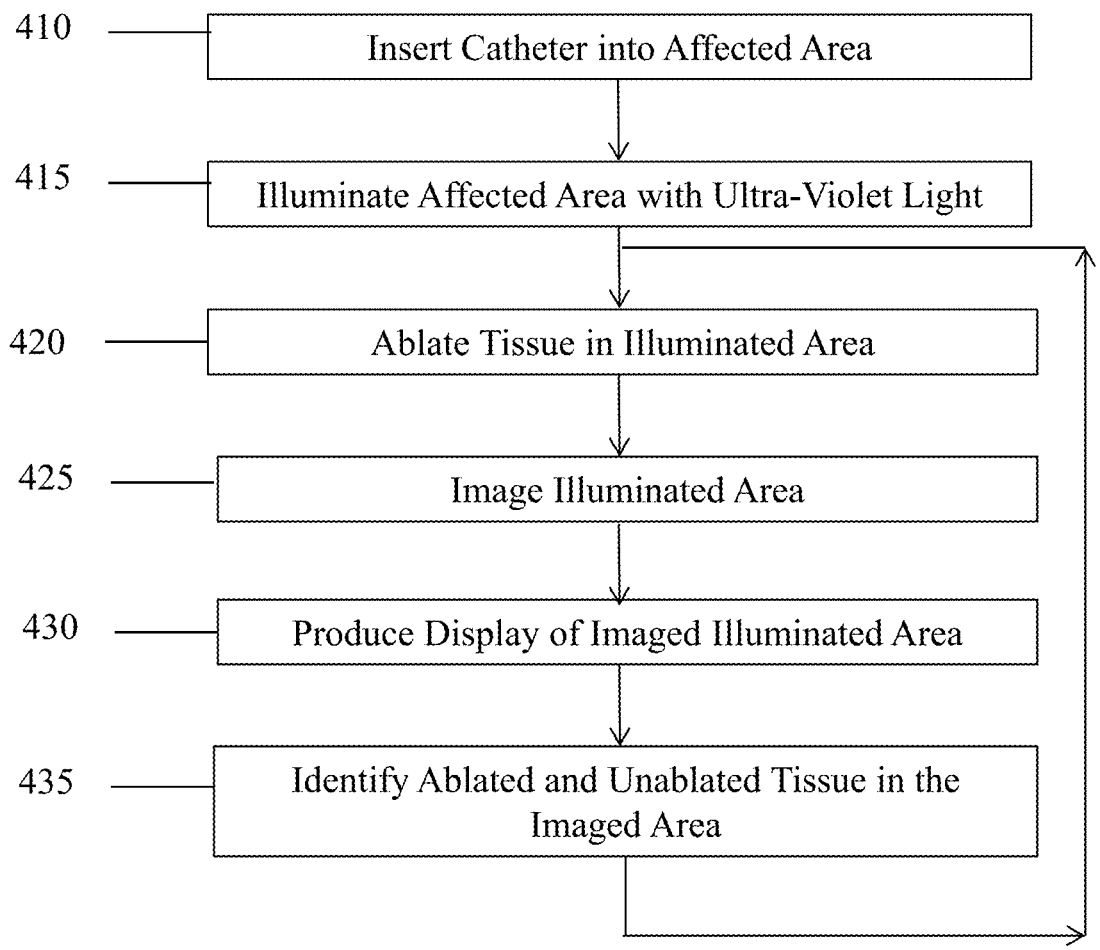
FIG. 4A, FIG. 4B, FIGS. 4C and 4D show flow diagrams of a method in accordance with the present disclosure.

In reference to FIG. 4A, operation of the systems and methods of the present disclosure are illustrated. It is noted that systems and methods include the analysis of multiple wavelengths of light reflected from acutely ablated atrial tissue and follow-up spectral imaging analysis, wherein a hyperspectral imaging device is used as a tool to distinguish between ablated and unablated atrial tissue based on subtle spectral differences between the two. At least one aspect of the systems and methods includes spectral unmixing of hyperspectral cube datasets to reveal sites of thermal ablations and gaps between them.

Initially, step 410 of FIG. 4A discloses inserting a catheter into affected area. Step 415 of FIG. 4A includes illuminating the affected area with the light source. As used herein, "light" refers generally to electromagnetic radiation of any wavelength, including the infrared, visible, and ultraviolet portions of the spectrum. A particularly portion of the spectrum of illuminating light can be the portion which produces the largest spectral differences between reflected light coming out of the native (non-ablated) and ablated tissue. To illuminate the surface, the catheter is inserted into the area of heart tissue affected by the atrial fibrillation, such as the pulmonary vein/left atrial junction or another area of the heart. Blood is removed from the visual filed, for example, by the balloon. A transparent balloon surrounding the fiber optic waveguide can be used to displace the blood at the pulmonary vein/left atrial junction. The affected area may be illuminated by light from the light source and the optical fiber or another illumination device.

Step 420 of FIG. 4A includes ablating the tissue in the illuminated area. It is possible while collecting the reflected light to the imaging device to also conduct ablation procedures. For example, for atrial fibrillation ablation a tissue in the illuminated area may be ablated using an ablation device, either before or after illumination. Either point-to-point RF ablation or cryoablation or laser or other known ablation procedures may be employed using the systems of the present disclosure. Ablation proceeds by threading the tip through the central lumen of the catheter or outside the catheter. After the procedure, the ablation tip may be retracted. In some embodiments, an ablation tip may be incorporated into the catheters disclosed herein.

Step 425 includes taking an image of the illuminated area, collecting and directing the reflected light to an imaging device. The latter can be done via a fiberoptic cable leading to a camera or directly by a small imaging chip.

Step 430 of FIG. 4A includes producing a display of the imaged illuminated area. Step 435 of FIG. 4A includes identifying ablated and unablated tissue in the imaged area using changes in spectral signature between the ablated and unablated tissue, as described above.

The application software, executing on the computer system by the processor or computer, can provide the user with an interface to the physician. Some of the main functions can include: a laser control, a camera control, an image capture, an image conditioning (brightness and contrast adjustment, etc.), a lesion identification, a lesion depth analysis, a procedure event recording, and a file manipulation (creation, editing, deleting, etc.).

Figure 4B:
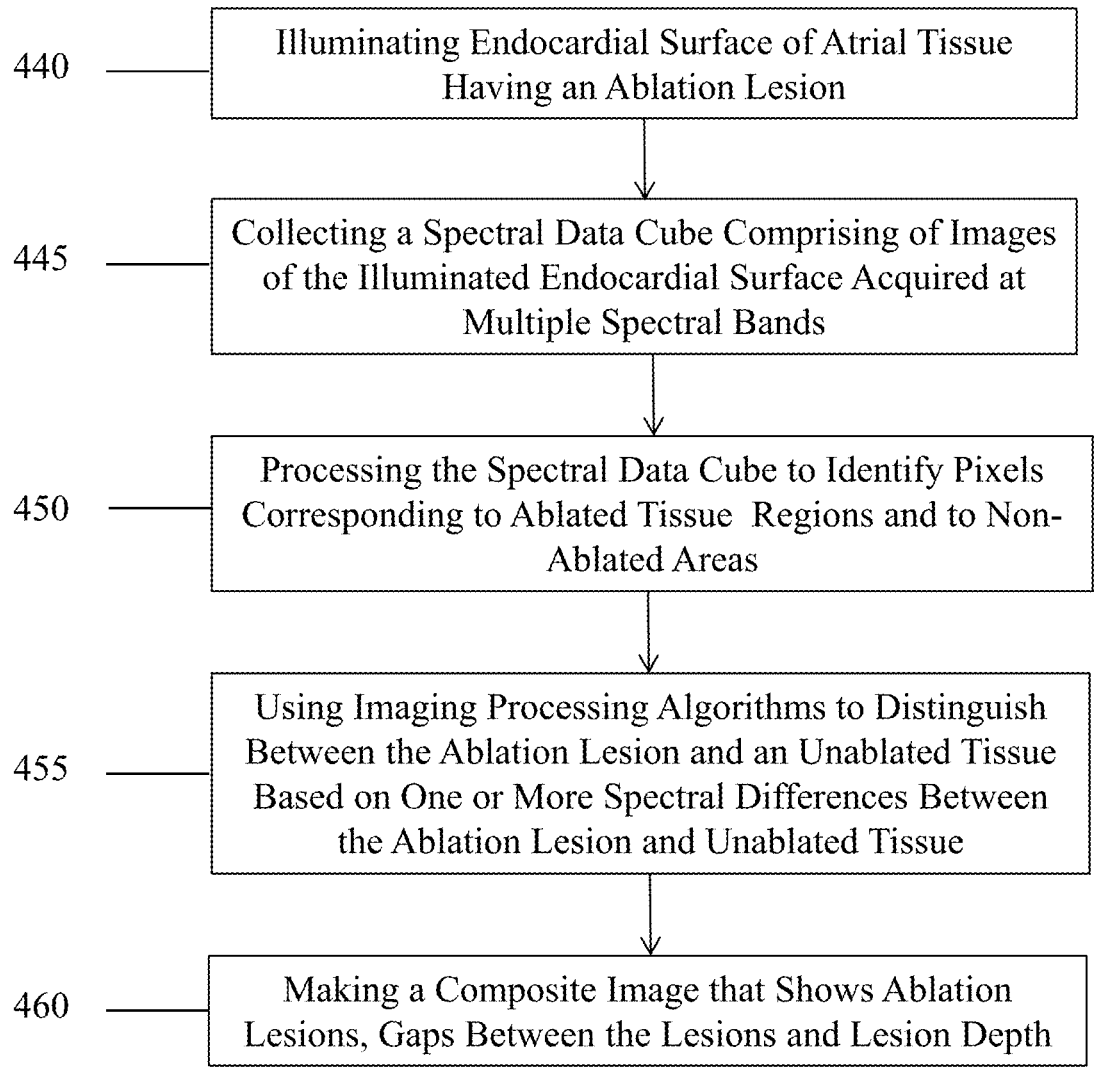

FIG. 4B is a flow chart of an exemplary method for constructing a HSI image of the ablated tissue. Step 440 of FIG. 4B includes illuminating at a specific wavelength endocardial surface of the atrial tissue that has the ablation lesion. Step 445 of FIG. 4B includes collecting a spectral data cube comprising of images of the illuminated endocardial surface acquired at multiple spectral bands. Specifically collecting data to form a three dimensional dataset (spectral data cube or hyperspectral data cube (HSDC)) that comprises of images of illuminated endocardial surface acquired at multiple spectral bands. Step 450 of FIG. 4B includes processing the spectral data cube to identify pixels corresponding to ablated tissue regions and to non-ablated areas. Specifically, the processing of the spectral data to identify pixels corresponding to the ablated tissue regions and the non-ablated areas. The latter is composed of three dimensions: two spatial (X, Y) and one spectral ($\lambda$). HSDC can complied from two spatial dimensions (X, Y) acquired simultaneously while the spectrum is built by sequentially scanning through wavelengths ($\lambda$) using a tunable optical band-pass filter. Alternatively HSDC can be compiled from one spatial and one spectral dimension (Z, X) acquired simultaneously, while the HSDC is built by sequentially scanning second spatial dimension (Y).

Step 455 of FIG. 4B includes using imaging processing algorithms to distinguish between the ablated lesion and an unablated tissue based on one or more spectral differences between the ablated lesion and unablated tissue. Specifically, classifying spectra from each pixel into different subsets using principal component analysis or related mathematical algorithms referred thereafter as spectral unmixing to distinguish between the ablated lesion and an unablated tissue based on one or more spectral differences between the ablated lesion and unablated tissue. Alternatively, spectra can be classified based on match with pre-existing spectral libraries. The spectrum of each pixel is then assumed to be a linear combination of pre-defined spectra and least squares approach is taken to fit these spectra to the observed pixel spectrum.

Step 460 of FIG. 4B includes making a composite image that shows ablation lesions, gaps between the lesions and lesion depth. Further, constructing an abundance map of each type of tissue, i.e. ablated vs unablated, collagen vs muscle, to display the fractional amount of its presence at each pixel. Thus, making a composite image that shows ablation lesions, gaps between the lesions and the lesion depth.

Figure 4C:
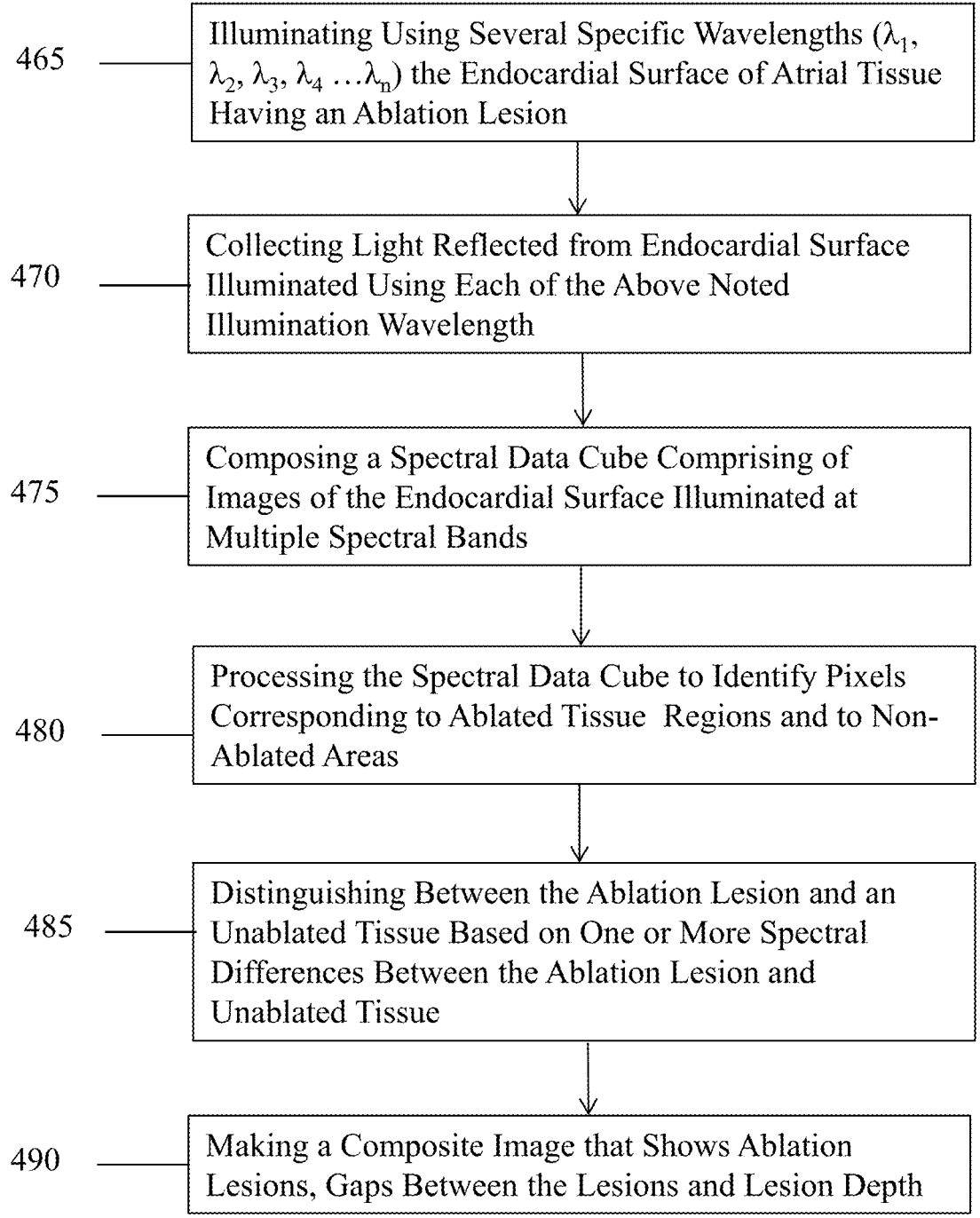

FIG. 4C illustrates another exemplary method of the present disclosure. Step 465 of FIG. 4C discloses illuminating using several specific wavelengths ($\lambda_1, \lambda_2, \lambda_3, \lambda_4 \ldots \lambda_n$) the endocardial surface of atrial tissue having an ablation lesion. Step 470 of FIG. 4C discloses collecting light reflected from the endocardial surface illuminated using each of the above noted illumination wavelength. Step 475 of FIG. 4C discloses composing spectral data cube comprising of images of the endocardial surface illuminated at multiple spectral bands. Step 480 of FIG. 4C discloses processing the spectral data cube to identify pixels corresponding to ablated tissue regions and to non-ablated areas. Step 485 of FIG. 4C discloses distinguishing between the ablated lesion and an unablated tissue based on one or more spectral differences between the ablated lesion and unablated tissue. Step 490 of FIG. 4C discloses making a composite image that show ablation lesions, gaps between the lesions and lesion depth.

Figure 4D:
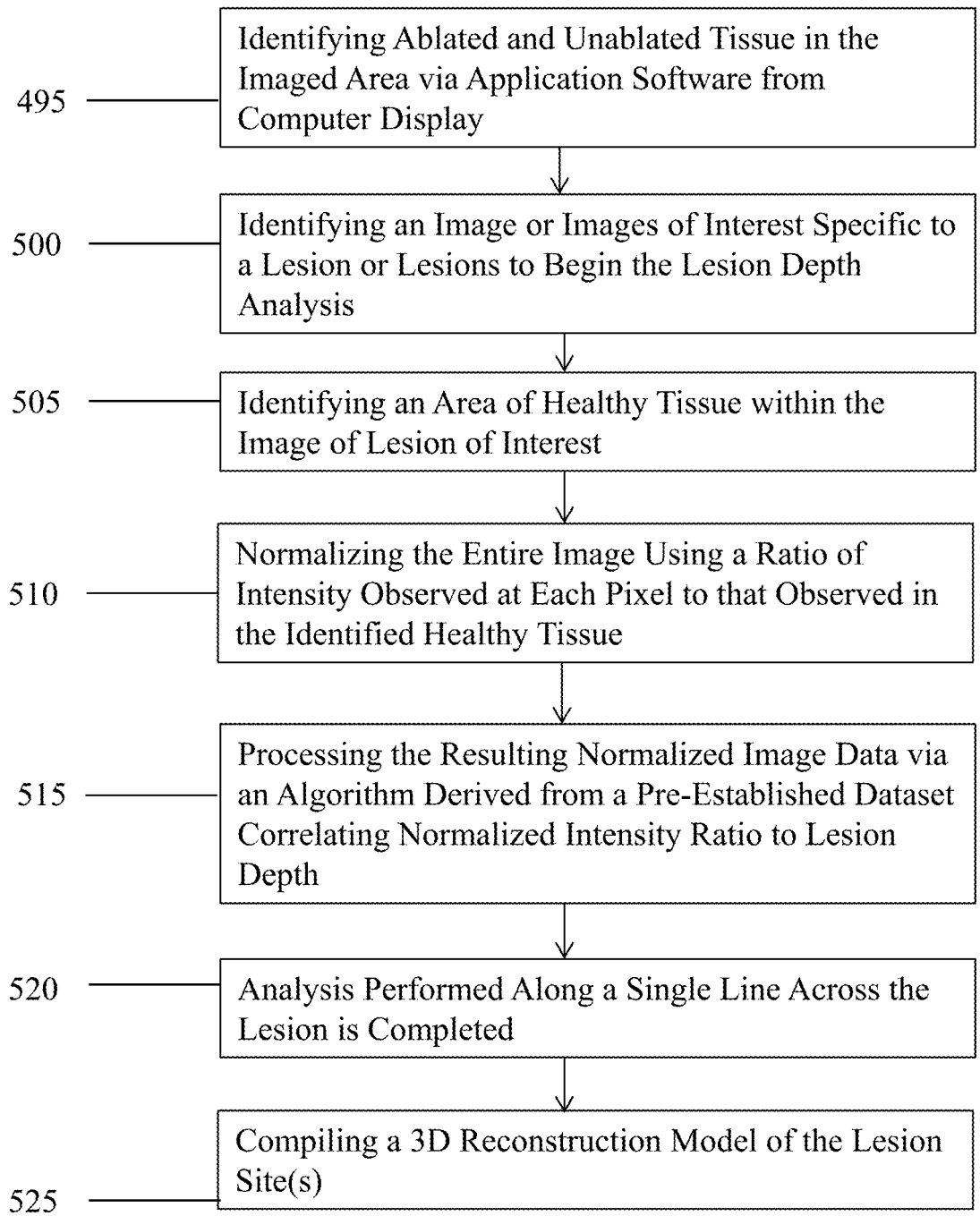

FIG. 4D illustrates a flow chart of the determining the lesion depth process. In some embodiments, a depth map of the ablated lesions may be constructed, as shown, for example, in FIGS. 13A-13B. Step 495 of FIG. 4D discloses identifying ablated and unablated tissue in the imaged area via application software from computer display. Step 500 of FIG. 4D discloses identifying an image or images of interest specific to a lesion or lesions to begin the lesion depth analysis. Step 505 of FIG. 4D discloses identifying an area of healthy tissue within the image of lesion of interest. By way of a non-limiting example, due to changes in spectral changes of ablated tissue, the lesion site may have a dark appearance which may become more intense as lesion depths increases, gaps or healthy tissue having lighter appearance. Once the lesion or lesions are identified, they are selected for lesion depth analysis. Step 510 of FIG. 4D discloses normalizing the entire image using a ratio of intensity observed at each pixel to that observed in the identified healthy tissue. Step 515 of FIG. 4D discloses processing the resulting normalized image data via an algorithm derived from a pre-established dataset correlating normalized intensity ratio to lesion depth.

Step 520 of FIG. 4D discloses the depth analysis performed along a single line across the lesion is completed. It is also possible that this can be done for just one single location in the lesions from information from a single location, a line or a region. Step 525 of FIG. 4D discloses repeating steps previous steps along different lines parallel to the initial line, so the depth data of each line compiles into a 3D reconstruction model of the lesion site(s). The depth analysis process performed along a single line across the lesion could be repeated as many times as needed along different lines parallel to the initial line, and the depth data of each line could be compiled into a 3D reconstruction model of the lesion site.

Figure 5A:
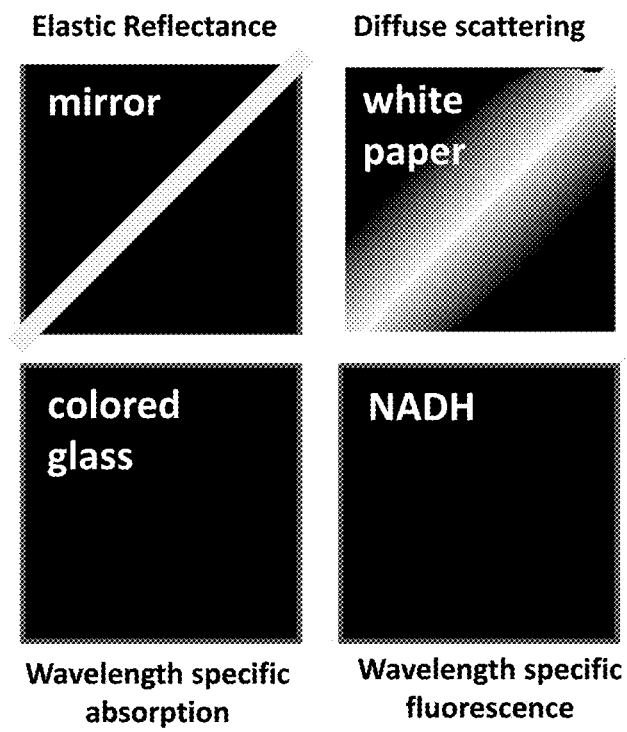
FIG. 5A illustrates an example of excitation-emission matrices (EEM) that provide information related to the physical phenomena behind spectral changes caused by ablation such as reflectance, scattering, absorption and fluorescence.
Figure 5B:
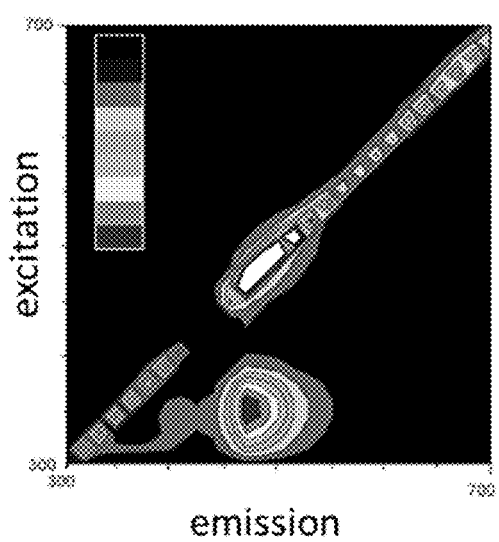
FIG. 5B illustrates an example of excitation-emission matrices (EEM) of a heart muscle.

FIG. 5A illustrates an example of excitation-emission matrices (EEM) that provides information related to the physical phenomena behind spectral changes caused by ablation such as reflectance, scattering, absorption and fluorescence. FIG. 5B illustrates an example of excitation-emission matrices (EEM) of a heart muscle.

Referring to FIG. 5A and FIG. 5B, human atria can have an average thickness of 2 mm ranging from 1-3 mm, wherein the layers of atrial muscle are sandwiched between layers of epicardiac and endocardial collagen. The latter can range from 50 micron to 1 mm in thickness.

Still referring to FIG. 5A and FIG. 5B, the biological tissues are heterogeneous in composition with spatial variations in optical properties. The scattering properties of tissues composed of cells and extracellular proteins, including elastin and collagen, are caused by the small-scale inhomogeneities and the large-scale variations in the structures they form. In addition, different tissue components have different fluorescence profiles. FIG. 5A shows the individual components of excitation-emission matrices (EEM), wherein the EEM can provide the full information from each individual component of the tissue. The 45 degree line across the EEM of FIG. 5A stands for reflected light. If displayed in linear form it shows the spectrum of reflected light, with its peaks corresponding to decreased absorption at specific wavelengths. Wherein, the diffuse scattering is represented by the width of the reflectance line. For example, the wider reflectance line the more diffuse scattering is observed at that specific wavelength (photons lose energy upon what is called non-elastic interactions so their wavelength decreases). Further, the peaks outside the 45 degree reflectance line stand for fluorescence of individual fluorophores. As noted above, FIG. 5A shows all three different components including reflected, scattered, and fluorescent light, collected from the cardiac muscle tissue. When intact, the cardiac muscle tissue has a significant amount of highly fluorescent NADH at 355/460 nm excitation/emission range.

Figure 6:
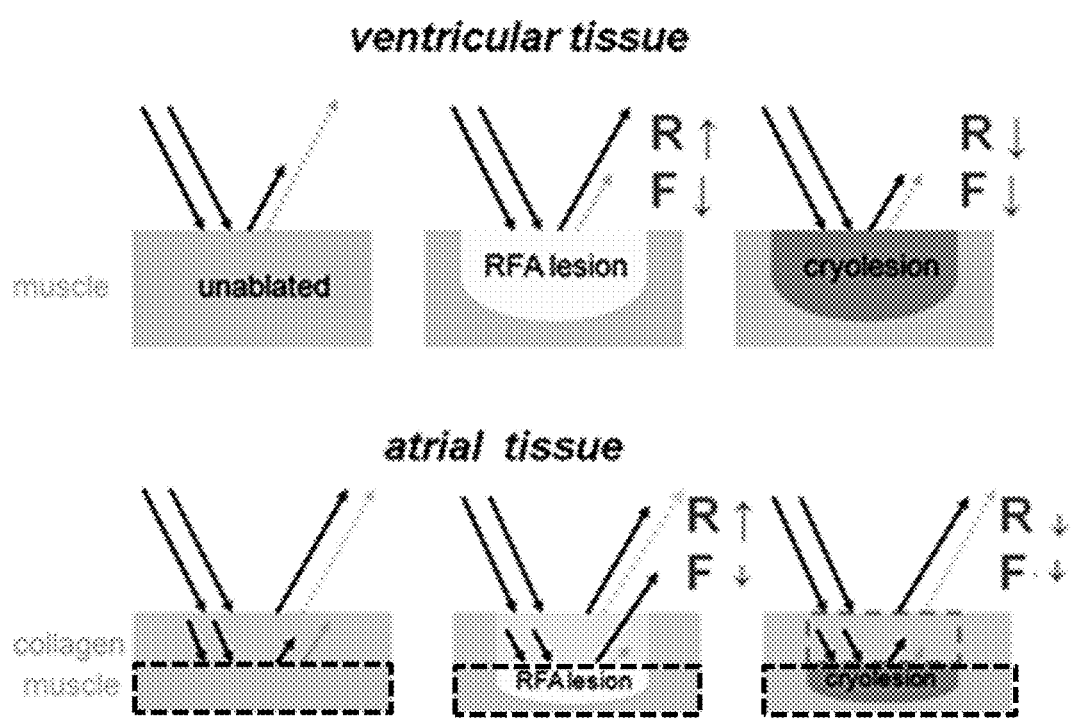
FIG. 6 illustrates some of the major differences in a way light interacts with radiofrequency ablation (RFA) lesions and cryo lesion in atrial tissue vs ventricular tissue.

FIG. 6 illustrates some of the major differences in a way light interacts with radiofrequency ablation (RFA) lesions and cryolesion in atrial tissue vs ventricular tissue. For example, thermal ablations can affect spectral properties of both collagen and underlying muscle tissue, including changes in their wavelength-specific absorption and fluorescence, and wavelength independent changes in tissue scattering. The direction and amplitude of these changes differ between specific subsets of conditions and types of thermal lesions. Yet, in all cases, ablation alters the spectral signature of tissue at the lesion site in a very distinct way. This allows for the use of a hyperspectral imaging approach to classify the pixels accordingly and to precisely identify the location, shape, size and depth of the ablation lesions, among other things.

Still referring to FIG. 6, regarding how the thermal ablations can affect the spectral properties of both collagen and underlying muscle tissue. It is noted that during atrial radiofrequency (RF) ablations, high temperatures denature and dehydrate surface collagen, which makes it more opaque and give it a slightly yellow hue. The RF energy also changes the spectral signature of the underlying muscle and lipid layers. The latter includes altered absorption spectrum and the loss of endogenous fluorophores, such as nicotinamide- and flavine-adenine-dinucleotides, lipofuscin, porphyrins and others. RF-induced ablation also causes protein coagulation which dramatically increases light scattering. Lastly, RF ablation dries both collagen and muscle layers increasing their optical density. All together, these changes lead to altered spectral signature enabling Hyperspectral Imaging (HSI) based identification of atrial ablation lesions throughout wide range of wavelengths, including ultraviolet, visible and infrared range. Specific changes include a distinct increase in diffuse reflectance across most of the visible range with the most occurring between 520-600 nm as well as a change in fluorescence (365 nm excitation/450 nm emission range) which corresponds to a decrease in NADH fluorescence.

Figure 7A:
FIG. 7A and FIG. 7B illustrate the difference in the left and the right atrial tissue appearance of an opened excised porcine atria, wherein the left atria image illustrates significantly higher layers of endocardial collagen as compared to the right atria image of an animal or human.
Figure 7B:
Figure 7C:
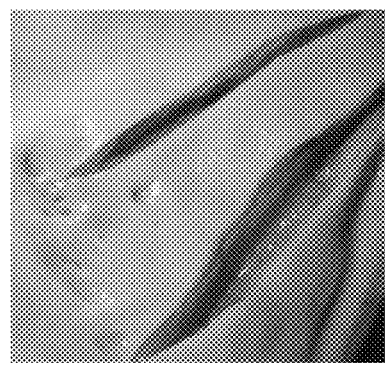
FIG. 7C and FIG. 7D illustrate an endocardial surface of an excised fresh human atria.
Figure 7D:
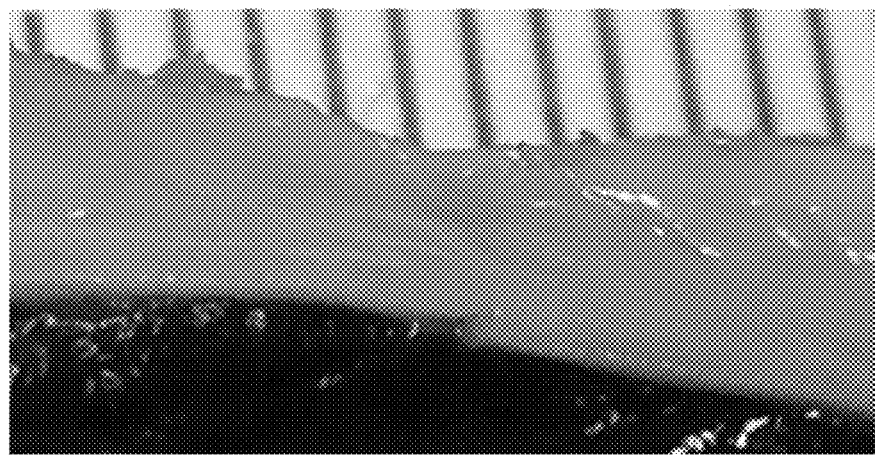

Regarding the collagen and underlying muscle tissue note above, FIG. 7A and FIG. 7B illustrate the difference in the left and the right atrial tissue appearance of an opened excised porcine atria. Wherein the left atria image illustrates significantly higher layers of endocardiac collagen as compared to the right atria image of an animal or human. FIG. 7C shows the endocardial surface of the excised fresh human atria with cuts to show muscle tissue beneath. FIG. 7D shows the human atrial tissue stained with triphenyltetrazolium chloride (TTC), wherein cross sections show darkly stained muscle layers and white collagen layer on the endocardial side.

However, certain wavelengths of light used for illumination and image acquisition can be more efficient than others as far as the ability of HSI approach to reveal ablation sites with high signal-to-noise ratio.

Wavelength Range (450 nm to 700 nm). When muscle tissue is RF-ablated, its color turns from red-brown to yellow-white hue. This can be easily seen by eye or recorded using color camera. In atrial tissue, however, muscle is covered by 0.1 mm to 0.5 mm thick collagen layer (see FIG. 7A and FIG. 7C). The latter obscures the ablation induced changes in the color of the muscle making RF lesion visually undetectable. Yet, very slight changes in hue and optical density provide sufficient spectral information to delineate the lesions using incandescent illumination and/or white light sources. Either push-broom based or AOTF based HSI imaging systems provide high fidelity lesion identification, as described in more detail below.

Offset Acquisition. According to aspects of the present disclosure, the experiments suggest that scattering is one of the three major optical components, wherein absorption and fluorescence being the other two. Therefore, at least one aspect of the present disclosure discloses that the effective way for visualization of atrial RF lesions is to illuminate the ablated surface with wavelengths below the spectral range in which HSI hypercube is to be acquired. For example ablated tissue can be illuminated with 460 nm LED and light acquired from 500-600 nm range. Increased scattering raises the entire right shoulder of the spectra of the light returning to the detector, allowing high fidelity spectral unmixing. By excluding illumination wavelengths from HSI acquisition and analysis, one prevents less discriminate, yet very intense reflected light. The latter can mask the differences between unablated and ablated tissue sites.

Infrared range (650-900 nm). Thermal ablation increases the light scattering across the entire optical spectrum. Thus, acquiring HSI spectral hypercube when the sample is illuminated by an infrared source can also serve as a basis for lesion identification. There can be additional advantages of using longer wavelengths because of at least two main reasons. First, among many reasons, it increases penetration for both illuminating and scattered light enabling visualization of deeper layers of damaged muscle. Secondly, among many reasons, it enables one to use therapeutic window where light absorption by hemoglobin is minimal and therefore lesion visualization can be done without the need to fully displace blood between the fiberoptic and the tissue.

Ultraviolet A or UVA (330-400 nm). Another illumination range where HSI can show high efficiency to reveal thermal lesions in left atrial tissue is UVA (see FIGS. 11A-11F for data for porcine and FIGS. 12A-12D for human left atria. Short wavelength UVA photons that illuminate atrial tissue do not penetrate deep into collagen layer and therefore are not reaching the muscle layer beneath it. Instead, by employing wavelengths where collagen can be excited (330-400 nm range), one elicit autofluorescence of atrial collagen that illuminates muscle layers beneath it. The emission profile of collagen is rather broad (peaking at 390 nm and reaching 500 nm), therefore photons emitted from collagen layer have longer wavelengths and are capable of penetrating into muscle layer and back to the detector. The dramatically increases reflectance from the ablated muscle that lies beneath the collagen, elevating the right shoulder of the returning light spectrum. In addition, heat of RF ablation dries up and condenses the tissue, yielding an increase in collagen fluorescence (see FIGS. 12A-12D). These two factors add up allowing HSI to discriminate between unablated and ablated tissue when illuminated in UV range.

According to aspects of the present disclosure, the illumination wavelength can be anywhere in the UV range of about 350 nm to about 400 nm, preferably within can be about 360 nm to about 370 nm. It is possible the illumination wavelength can be anywhere in the visible range 400 nm to about 700 nm, preferably within about 400 nm to about 500 nm range. Further, the illumination wavelength can be anywhere in the IR range 700 nm to about 900 nm, preferably within about 700 nm to about 750 nm range.

According to aspects of the present disclosure, the illumination light contains continuous range wavelengths that can be anywhere in the UV range of about 350 nm to about 400 nm, preferably within can be about 360 nm to about 370 nm. It is possible that the illumination wavelength can be anywhere in the visible range 400 nm to about 700 nm, preferably within about 400 nm to about 500 nm range. Further, the illumination wavelength can be anywhere in the IR range 700 nm to about 900 nm, preferably within about 700 nm to about 750 nm range.

According to aspects of the present disclosure, the illumination light can be within about 350 nm to about 380 nm range while collected light can be between about 400 nm and 700 nm range, preferably within about 400 nm and 500 nm range. Further, the illumination light can be in the visible range of about 400 nm to about 700 nm), while collected light can also be in the same range of about 400 nm to about 700 nm). It is possible the illumination light can be in the infrared range of about 700 nm to about 900 nm, while collected light is in the same range of about 700 nm to about 900 nm.

According to aspects of the present disclosure, the wavelength of illuminating light can be below the acquisition range by between about 10 nm and about 50 nm, including but limited to examples such as about 360 nm: about 370 nm to about 470 nm, about 370 nm: about 400 nm to about 480 nm, about 450 nm: about 500 nm to about 600 nm.

According to aspects of the present disclosure, the filtering can have an emission from the illuminated heart tissue using a set of individual bandpass filters, including but not limited to about 460/25 nm, about 500/25 nm, and about 540/25 nm, wherein using an acousto-optical filter in front of the camera tunable to a specified range, including but not limited to about 420 nm to about 720 nm, and about 45 nm to about 900 nm.

According to aspects of the present disclosure, the detecting light emitted from the illuminated heart tissue can include an emission comprising of fluorescence, reflectance and scattering components with fluorescence being the most different between ablated and unablated sites within about 400 nm to about 500 nm range, and with reflectance being most different between ablated and unablated sites within about 450 nm to about 600 nm range, and with diffuse reflectance being most different between ablated and unablated sites across visible spectra within about 550 nm to 600 nm range.

According to aspects of the present disclosure, the constructing a depth map of the ablated lesion from the image can be accomplished by using a density of the pixels that have target spectra, i.e. being ablated tissue, as an indicator of lesion depth, wherein the intensity of grey levels of each pixel can enable then to create a 3D map.

According to aspects of the present disclosure, the identifying the ablated lesion as a lesion created by radiofrequency and the setting of the illumination wavelength can be between about 400 nm to about 700 nm and the acquisition wavelength to about 400 nm to about 700 nm. Further, the identifying of the ablated lesion as a lesion created by cryoablation and setting the illumination wavelength can be between about 350 nm to about 400 nm and the acquisition wavelength to about 380 nm to about 500 nm. Further still, in identifying whether the ablated lesion was created by radiofrequency or cryoblation and, if the ablated lesion was created by radiofrequency, setting the illumination wavelength can be between about 400 nm to about 700 nm and the acquisition wavelength can be about 400 nm to about 700 nm, or, if the ablated lesion was created by cryoblation, setting the illumination wavelength can be between about 350 nm to about 400 nm and the acquisition wavelength can be between about 380 nm to about 500 nm.

According to aspects of the present disclosure, the spectral ranges and types of camera used can be varied. In some embodiments, both UV and white light illumination with hyperspectral analysis of reflected spectra can work to visualize RF lesions. UV illumination combined with the hyperspectral analysis of fluorescence is a better approach to visualize cryolesions. And because fluorescence intensity is several orders of magnitude less compared to the intensity of reflected light, cryolesion visualization requires hyperspectral cameras more sensitive in the near-UV range (350-500 nm), while RF lesions can be observed using less sensitive hyperspectral cameras that collect reflected light in 400 nm-700 nm range. Therefore, both illumination sources as well as types of camera might need to be different for the two types of ablation surgeries, despite the fact that the ultimate result of either cryo or RF ablation are lesions of necrotic myocardium. By way of a non-limiting example, the following settings may be used.

components. FIG. 10E shows a graph of the raw and normalized reflectance spectra, where the tissue was illuminated with incandescent white light, the reflected light was acquired within 450 nm to 750 nm range with 20 nm steps. FIG. 10F illustrates an overlay of two individual HSI components, the collagen 910 and the lesions 900.

Figure 11A:
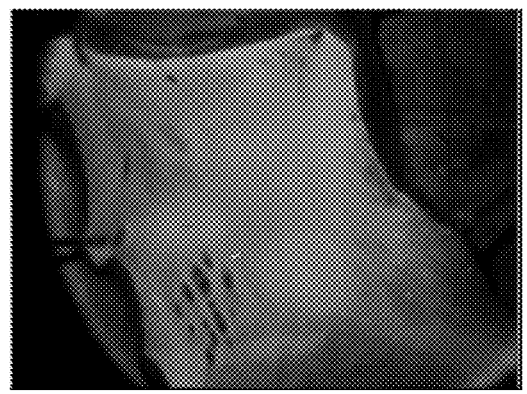
FIG. 11A, FIG. 11B, FIG. 11C and FIG. 11D illustrate an excised porcine left atria with three RF lesions.
Figure 11B:
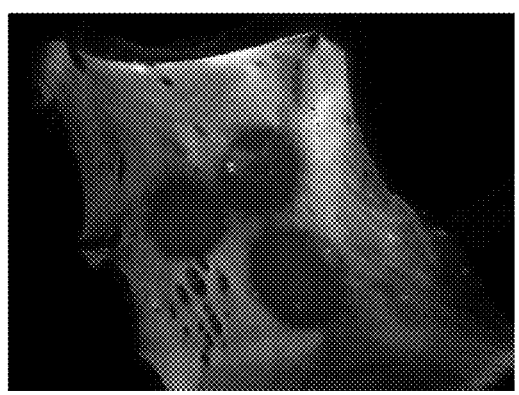
Figure 11C:
Figure 11D:
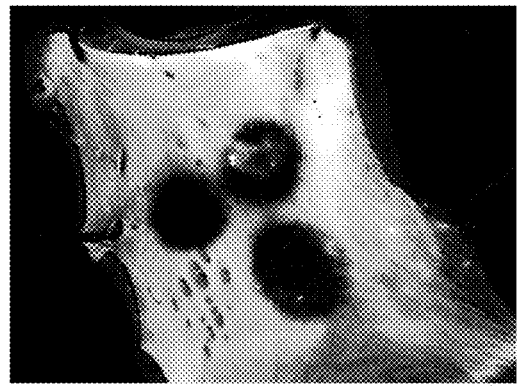

FIG. 11A, FIG. 11B, FIG. 11C and FIG. 11D illustrate an excised porcine left atria with three RF lesions. FIG. 11A shows a visual appearance of tissue under UV illumination, FIG. 11B shows a color coded HSI composite image, and FIG. 11C and FIG. 11D show individual components revealed by principal component analysis. FIG. 11C shows the individual components revealed by principal component analysis including Lesion component. FIG. 11D shows the individual components revealed by principal component analysis including non-ablated component.

Figure 11E:
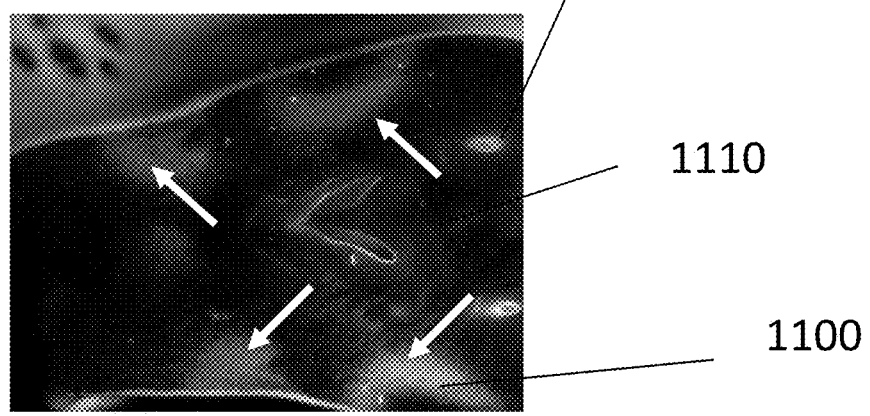
FIG. 11E shows tissue that was crosscut through line 1130 in FIG. 11C shown above and folded in half in order to expose ablated muscle tissue (see arrows) beneath the collagen layer, showing muscle 1110, ablated muscle 1100 and collagen 1120.
Figure 11F:
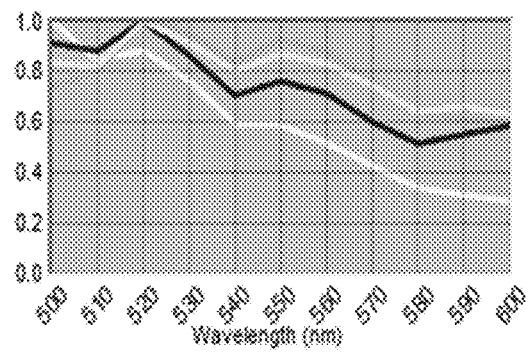
FIG. 11F shows the corresponding target spectra of FIG. 11E, wherein the tissue was illuminated with 365 nm LED UV light, and the reflected light was acquired from 420 nm to 600 nm range using 10 nm steps.

FIG. 11E shows tissue that was crosscut through line 1130 in FIG. 11C shown above and folded in half in order to expose ablated muscle tissue (see arrows) beneath the collagen layer. Wherein a color coded HSI composite image shows the aspects of the tissue, showing muscle 1110, ablated muscle 1100 and collagen 1120. Further, FIG. 11F shows the corresponding target spectra of FIG. 11E, wherein

| LESION TYPE | Type of signal | Illumination | Illumination wavelength | Images acquired at | Camera sensitivity |
|---|---|---|---|---|---|
| Radiofrequency | Reflectance | White light | 400 nm-700 nm | 400 nm-1000 nm | medium |
| Cryoablation | Fluorescence | UV light source | 350 nm-400 nm | 380 nm-500 nm | high |

Figure 8A:
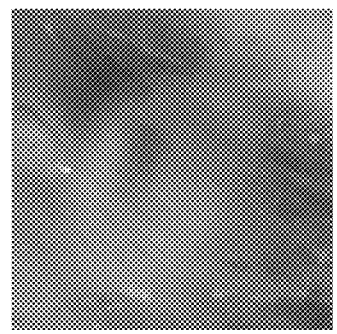
Figure 8B:

FIG. 8A, FIG. 8B, FIG. 8C and FIG. 8D illustrate the ability of Hyperspectral Imaging (HSI) system to reveal lesion boundaries. FIG. 8A shows an example of visual appearance of an RFA lesion on the endocardial surface of canine left atria. Although lesion can be visually seen it has poorly defined boundaries. FIG. 8B shows a visual appearance of two radiofrequency ablation lesions on the endocardial surface of excised porcine left atria. Again, boundaries of the lesions cannot be clearly define.

Figure 8C:
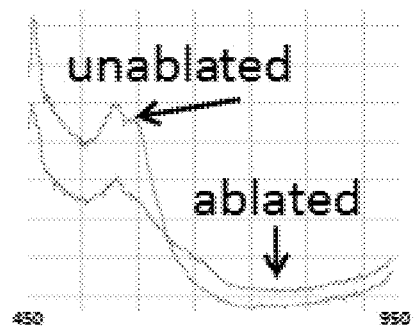
Figure 8D:
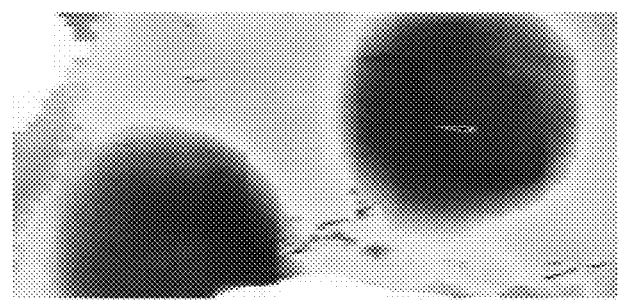

FIG. 8C and FIG. 8D show the porcine sample shown in FIG. 8B that was imaged by a custom push-broom HSI system comprised of a Specimen spectrograph and an Andor iXon CCD built by Middleton Research. Spectral profiles from unablated and ablated areas of endocardial surface of porcine left atria differed (FIG. 8C) enabling effective unmixing of hyperspectral cube. The resulting HSI data cube was analyzed using principal component analysis performed by UmBio Evince software package, yielding a pseudo color composite HSI image with two clearly delineated lesions (FIG. 8D).

Figure 9A:
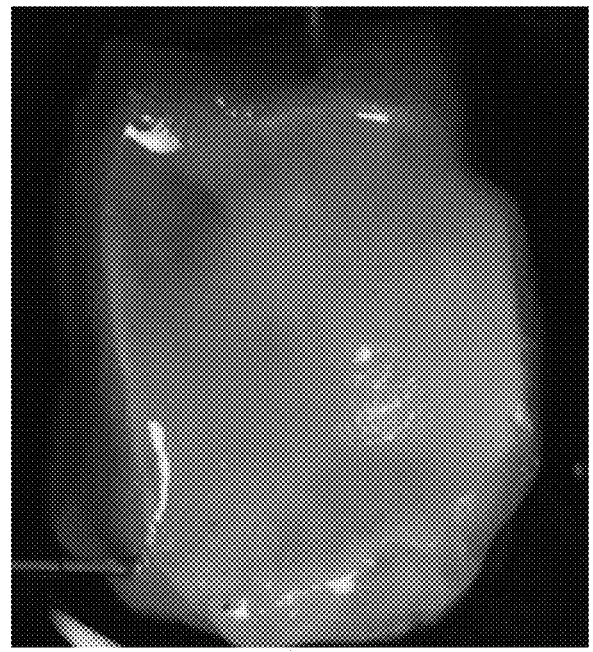
FIG. 9A and FIG. 9B illustrate an excised porcine left atria with two RF lesions imaged using Perkin-Elmer Nuance FX multispectral imaging system equipped with AOTF filter in front of the camera.
Figure 9B:
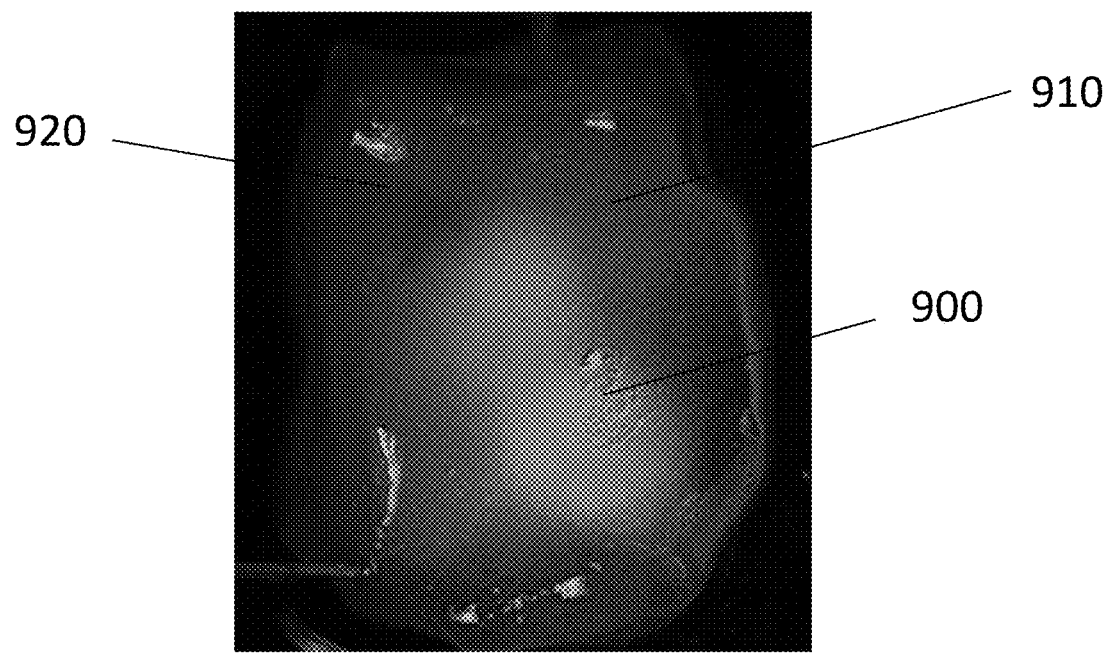

FIG. 9A and FIG. 9B illustrate an excised porcine left atria with two RF lesions imaged using a Perkin-Elmer Nuance FX multispectral imaging system equipped with a AOTF filter in front of the camera. FIG. 9A shows a visual appearance of the tissue, and FIG. 9B shows the individual components revealed by HSI cube principal component analysis (900 is the lesion sites, blue the collagen and red is muscle). The tissue was illuminated with an incandescent white light, wherein the reflected light was acquired within a 450 nm-950 nm range using a 20 nm step.

Figure 10A:
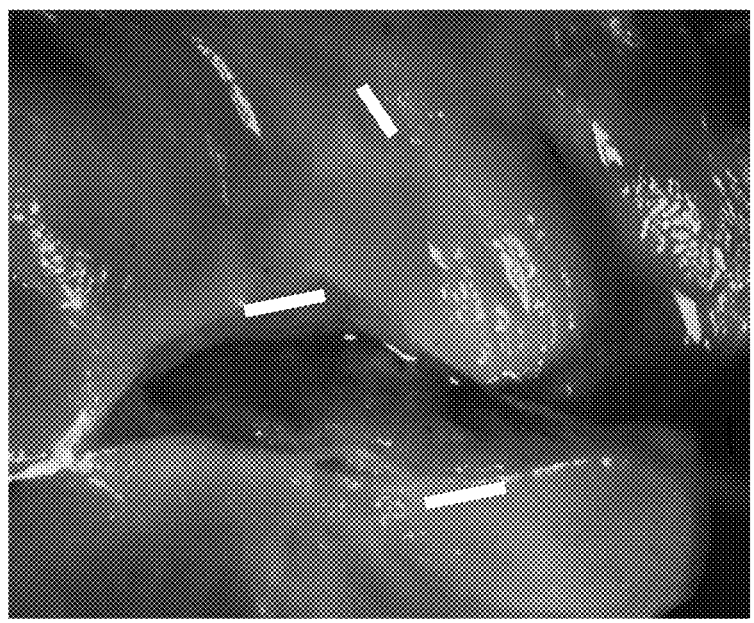
FIG. 10A, FIG. 10B, FIG. 10C and FIG. 10D illustrate an excised human left atria with four RF lesions.
Figure 10B:
Figure 10C:
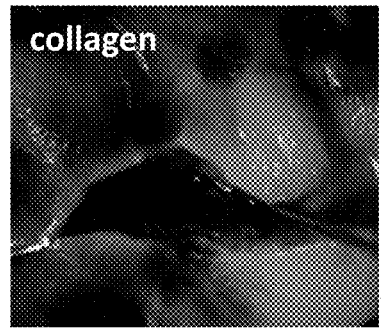
Figure 10D:
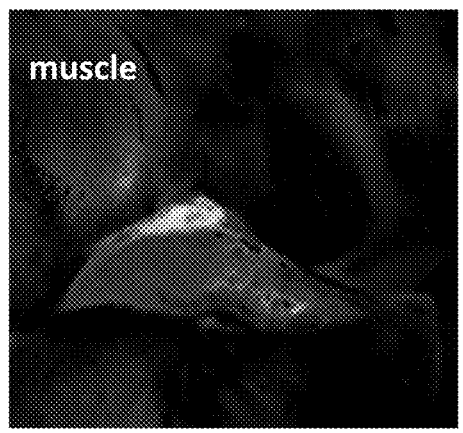
Figure 10E:
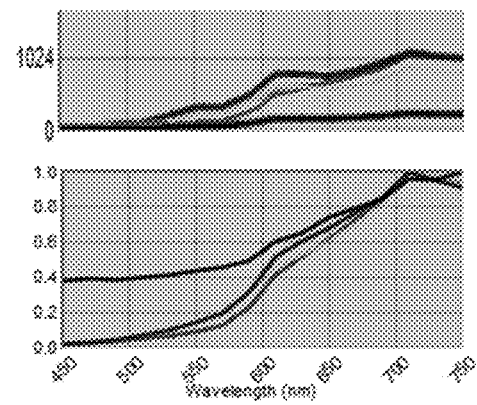
FIG. 10E shows a graph of the raw and normalized reflectance spectra, where the tissue was illuminated with incandescent white light, the reflected light was acquired within 450 nm to 750 nm range with 20 nm steps.
Figure 10F:
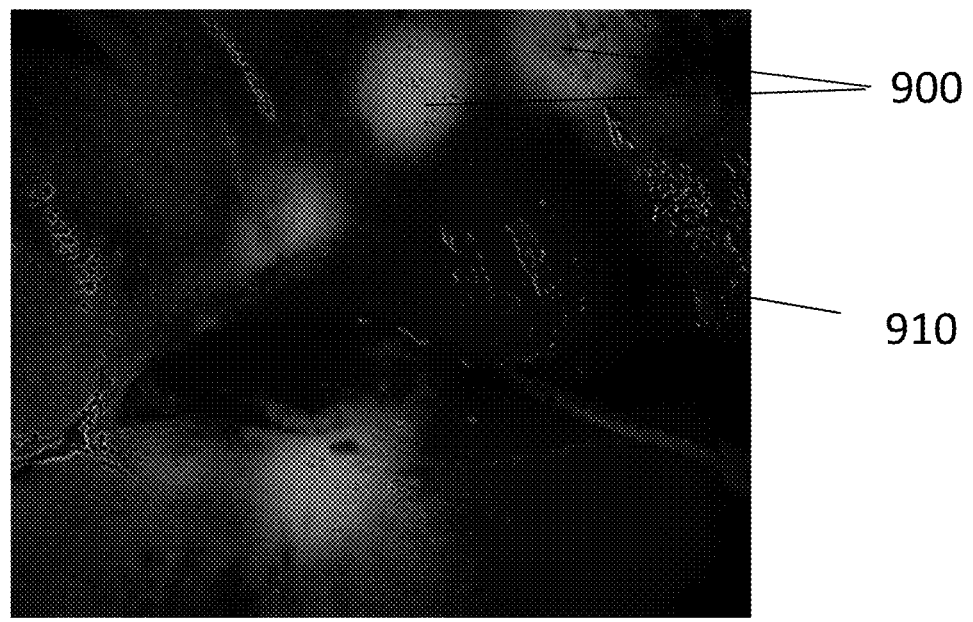
FIG. 10F illustrates an overlay of two individual HSI components, collagen 910 and the lesions 900.

FIG. 10A, FIG. 10B, FIG. 10C and FIG. 10D illustrate an excised human left atria with four RF lesions. FIG. 10A illustrates a visual appearance of the tissue with regions of interest used to decompose a HSI cube into individual components.

the tissue was illuminated with 365 nm LED UV light, and the reflected light was acquired from 420 nm to 600 nm range using 10 nm step.

In regard to chronic Radio Frequency (RF) lesions, HSI can be used for visualization of healed lesions from previously performed RF surgeries, as well as in addition to real-time in-surgery visualization of acute RF lesions and gaps between them. This is because collageneous scar formed at the site of the successful ablation has a very different spectral signature that surrounding muscle tissue. Therefore, HSI can reveal the sites of previous RF ablations allowing physician to target the remaining gaps and to avoid repetitively burning previously ablated areas (the latter can lead to excessive scarring, loss of atrial compliance and/or pulmonary vein stenosis).

In regard to using cryo ablation procedures, cryo ablation procedures is gaining popularity as an alternative means to destroy tissue near the ectopic sources. It creates more 'clean' lesions as compared to the RF procedures and has less incidences of post-surgical pulmonary stenosis. The cryolesions also are more defined and have less scar formation, in part because, in contrast to RF, cryoablation does not lead to thermal coagulation of collagen and underlying muscle layers. Instead it destroys cells by formation of ice crystals that tear membranous structures. In contrast to RF ablation, cryoablation of muscle yields in reduced light scattering across visible spectrum.

The above described unmixing of reflectance spectra that can resolve RF lesions, can be also applicable to visualization of cryolesions. Yet, because changes in scattering are less dramatic for cryolesions, HSI is likely to be less effective for visualization of cryolesions based on just change in tissue scattering. On the other hand, for cryolesions, the loss of muscle NADH and diminished reflectance produce changes in the SAME direction—i.e., both results in LOWERING the right shoulder of the returning light spectrum. In addition, if one looks at the spectral profile of the fluorescence, the fluorescence peaks of NADH and collagen can be clearly distinguished. Upon cryoablation, atrial muscle is destroyed and fluorescence of NADH diminishes, while collagen layer stays intact. Therefore while total decrease in returning light intensity is minimal, the spectral profile of the fluorescence coming from the lesion site changes. Use of spectral unmixing algorithms then allows one to identify the lesions and the gaps between them.

FIG. 12A, FIG. 12B, FIG. 12C and FIG. 12D show an image of excised human left atria with four RF lesions of different strengths. FIG. 12A shows a visual appearance of the tissue under incandescent illumination. FIG. 12B illustrates HSI identified lesions using UV illumination (365 nm LED source). FIG. 12C shows that under UV illumination lesions appears denser. One of the underlying spectral components is increased fluorescence intensity from ablated collagen due at least in part to RF caused loss of water content, as noted above. To illustrate this effect, the tissue of FIG. 12D was crosscut through line 1220, folded in half and imaged using the same settings. The red arrows point to increased intensity of collagen at the lesion sites. Additional spectral component can be change in color and increased scattering of underlying muscle shown in previous figure.

Figure 13A:
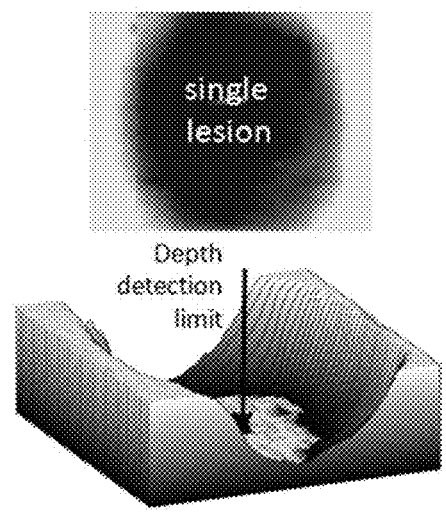
FIG. 13A and FIG. 13B, illustrate a porcine left atrial tissue with RF ablation lesions on the endocardial surface.
Figure 13B:
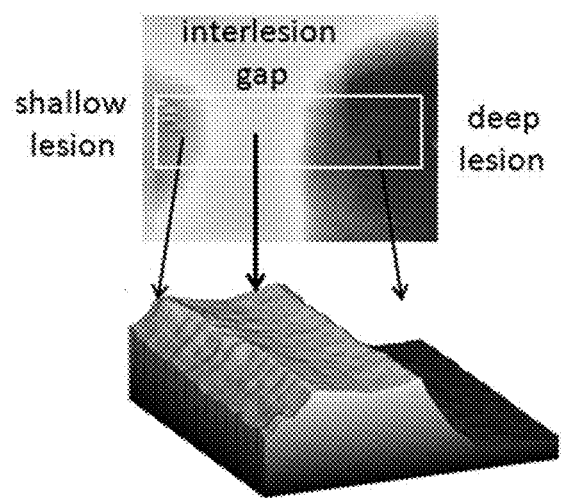

FIG. 13A and FIG. 13B, illustrate a porcine left atrial tissue with RF ablation lesions on the endocardial surface. FIG. 13A shows a single deep lesion and its 3D surface plot, and FIG. 13B illustrates two lesions of different depth with unablated tissue in between. Below is shown a 3D surface plot of the two lesions that shows the region of unablated tissue.

Regarding ablation lesions of FIG. 13A and FIG. 13B, ablation lesions must be of adequate depth and cause cell necrosis in a near transmural fashion while minimizing damage to non-cardiac structures. The mean left atrial wall thickness in humans is about 1.8 mm. HSI ability of detect lesion depth is inversely related to frequency of illuminating wavelength, with longer wavelengths (near infrared and infrared range) penetrating and sensing the deeper lesions. Changes in diffuse tissue reflectance caused by RF ablation are, in large part, result of increased transmural tissue dryness as water evaporates from the ablation site. Increased lesion depth therefore, results in more opaque appearance of the tissue. FIG. 13A and FIG. 13B show a reconstruction of a lesion depth from an HSI image. FIG. 13A displays a 3D depth profile of a deep RF lesion as well as gap between weak and strong lesion placed side by side as viewed in FIG. 13B.

It is contemplated that the systems and methods of the present disclosure relating to the approach of unmixing of spectral information from the areas that contain ablated tissue can be applied to the entire image made from multiple pixels or to limited number of individual pixels. It is possible that in an extreme case that there will be single a point measurement and a spectral analysis of the light collected using a contact-type catheter.

It is possible that the systems and methods of the present disclosure can be applied to any parts of the heart, including epicardial and endocardial surfaces of the right and left atria, endocardial and epicardial surfaces of the ventricles, as well as major vessels and valve structures.

Further, it is possible that the systems and methods of the present disclosure can be applied to identify different tissues and sites of ablation that are performed on various organs and parts of the human body, including, but not to limited to uterine lining (endometrial ablation) or cancer within several organs of the body, including the liver, kidneys, lungs, muscle or bone.

According to aspects of the present disclosure, the surface of tissue can include heart tissue. The surface of heart tissue can include an endocardial surface of atrial tissue. The illumination wavelength can be between about 350 nm and about 400 nm. The illumination wavelength can be between about 400 nm and about 700 nm. The illumination wavelength can be between about 700 nm and about 900 nm. The illumination wavelength can be below a range of acquisition wavelengths by between about 10 nm and about 50 nm.

According to aspects of the present disclosure, it is possible to include filtering light returning from the illuminated heart tissue using a set of bandpass filters. It is contemplated to include filtering light returning from the illuminated heart tissue using a tunable filter. It is possible to incorporate detecting a light returning from the illuminated heart tissue, that includes fluorescence, reflectance and scattering components, wherein the fluorescence component being detected at the acquisition wavelength between about 400 nm to about 500 nm, the reflectance component being detected at the acquisition wavelength between about 450 nm and about 700 nm, and the scattering component detected across the entire visible spectra.

According to aspects of the present disclosure, it is possible to include classifying each pixel of a digital image of the illuminated tissue as either ablated or unablated tissue. Wherein constructing a depth map of the ablation lesion can be from the image based on a bulk density of image pixels classified as ablated tissue.

According to aspects of the present disclosure, it is contemplated to further include identifying the ablated lesion as a lesion created by radiofrequency; and setting the illumination wavelength to between about 400 nm and about 700 nm and the acquisition wavelength to about 400 nm and about 700 nm. It is possible to further include identifying the ablated tissue created by cryoablation by setting the illumination wavelength to between 350-400 nm and the range of acquisition wavelengths to 380-500 nm. It is contemplated to further include identifying the ablated tissue created by radiofrequency by setting the illumination wavelength to between 350-400 nm and the range of acquisition wavelengths to 380-500 nm. Further, it is possible to include identifying ablation lesions created by other types of thermal ablations including laser, microwave or focused ultrasound induced lesion. It is contemplated to further include illuminating at one or more illumination wavelengths a specific wavelength or using wide band illumination with a known spectral distribution. It is possible to further include distinguishing between the ablation lesion and an unablated tissue based on one or more spectral differences of a pre-selected set of multiple spectral differences.

According to aspects of the present disclosure, it is contemplated to further include the collecting of the spectral data that includes one of a detector-based Hyperspectral Imaging (HSI) system, a detector-based HSI system using static devices with tunable filters, an alternative source-based HSI including a changeable wavelength of illuminating light or some combination thereof. It is possible to further include the collected spectra data can be one of matched to existing spectral libraries, subjected to a principal component analysis, subjected to related principal component analysis algorithms or some combination thereof.

In some aspects, there is provided a method for visualizing ablation lesions that includes illuminating at one or more illumination wavelengths a surface of tissue having an ablation lesion; collecting a spectral data set comprising spectral images of the illuminated tissue acquired at multiple spectral bands each at one or more acquisition wavelengths; distinguishing between the ablation lesion and an unablated tissue based on one or more spectral differences between the ablation lesion and unablated tissue; and creating a composite image of the tissue showing the ablation lesion and the unablated tissue.

In some aspects, there is provided a method for visualizing atrial ablation lesion that includes illuminating one or more discrete illumination wavelengths a surface of heart tissue having an ablation lesion; collecting a spectral data from the illuminated heart tissue; distinguishing between the ablation lesion and an unablated tissue based on one or more spectral differences between the ablation lesion and unablated tissue; and creating an image of the heart tissue illustrating ablated tissue and unablated tissue.

In some aspects, there is provided a system for imaging tissue that includes a catheter having a distal region and a proximal region; a light source; an optical fiber extending from the light source to the distal region of the catheter to illuminate a tissue having a lesion site in proximity to the distal end of the catheter; an image bundle for collecting light reflected from the illuminated tissue; a camera connected to the image bundle, the camera being configured to gather hyperspectral data comprising spectral images of the illuminated tissue acquired at multiple spectral bands or at each illumination wavelength; an image processing unit in communication with the camera, the unit being configured to distinguish between the ablation lesion and an unablated tissue based on one or more spectral differences between the ablation lesion and unablated tissue and creating an image of the heart tissue illustrating the ablated tissue and the unablated tissue.

In some aspects, there is provided a system for imaging heart tissue that includes an illumination device configured to illuminate a tissue having a lesion site; an imaging device configured to gather hyperspectral data; an image processing unit in communication with the imaging device, the image processing unit configured to processing gathered hyperspectral data to generate an image that reveals the lesion site, wherein the generated image enabling to distinguish between an ablation lesion and an unablated tissue based on one or more spectral differences between the ablation lesion and unablated tissue and creating an resulting image of the heart tissue illustrating the ablated tissue and the unablated tissue.

The foregoing disclosure has been set forth merely to illustrate various non-limiting embodiments of the present disclosure and is not intended to be limiting. Since modifications of the disclosed embodiments incorporating the spirit and substance of the disclosure may occur to persons skilled in the art, the presently disclosed embodiments should be construed to include everything within the scope of the appended claims and equivalents thereof.

What is claimed is:

1. A method for visualizing ablation lesions, the method comprising:
    illuminating at one or more illumination wavelengths a surface of tissue having one or more ablation lesions;
    collecting a spectral data set comprising spectral images of the illuminated surface of the tissue acquired at multiple spectral bands each at one or more acquisition wavelengths;
    extracting and normalizing spectra from individual pixels of the spectral data set,
    forming one or more individual component images based on spectral unmixing of the normalized spectra, wherein an individual component image is a two-dimensional map of a relative abundance of a specific spectrum within each pixel; and
    combining the individual component images showing ablated and unablated tissue into a pseudocolor composite image using a different color for each individual component image, the pseudocolor composite image visually distinguishing the one or more ablation lesions from the unablated tissue based on one or more spectral differences between the ablation lesions and the unablated tissue;
    wherein the pseudocolor composite image shows the one or more ablation lesions, the unablated tissue, and any gaps between ablation lesions.

2. The method of claim 1 wherein the surface of tissue is an endocardial surface of atrial tissue.

3. The method of claim 1 wherein the one or more illumination wavelengths are between about 350 nm and about 400 nm.

4. The method of claim 1 wherein the one or more illumination wavelengths are between about 400 nm and about 700 nm.

5. The method of claim 1 wherein the one or more illumination wavelengths are between about 700 nm and about 900 nm.

6. The method of claim 1 wherein the one or more illumination wavelengths are below a range of acquisition wavelengths by between about 10 nm and about 50 nm.

7. The method of claim 1 further comprising filtering light returning from the illuminated tissue using a set of bandpass filters.

8. The method of claim 1 further comprising filtering light returning from the illuminated tissue using a tunable filter.

9. The method of claim 1 further comprising detecting a light returning from the illuminated tissue, the detected light including fluorescence, reflectance and scattering components, wherein the fluorescence component being detected at the acquisition wavelength between about 400 nm to about 500 nm, the reflectance component being detected at the acquisition wavelength between about 450 nm and about 700 nm, and the scattering component detected across the entire visible spectra.

10. The method of claim 1 further comprising classifying each pixel of a digital image of the illuminated tissue as either ablated or unablated tissue.

11. The method of claim 10 further comprising constructing a depth map of the ablation lesion from the image based on a bulk density of the pixels of the digital image classified as ablated tissue.

12. The method of claim 1 further comprising identifying the ablated lesion as a lesion created by radiofrequency; and setting the illumination wavelength to between about 400 nm and about 700 nm and the acquisition wavelength to about 400 nm and about 700 nm.

13. The method of claim 1 further comprising identifying the ablation lesion as a lesion created by cryoablation or radiofrequency; and setting the illumination wavelength to between about 350 nm to 400 nm and a range of acquisition wavelengths to about 380 nm to 500 nm.

14. The method of claim 1 further comprising illuminating at one or more illumination wavelengths a specific wavelength or using wide band illumination with a known spectral distribution.

15. The method of claim 1 further comprising distinguishing between the ablation lesion and an unablated tissue based on one or more spectral differences of a pre-selected set of multiple spectral differences.

\* \* \* \* \*